(12) United States Patent
Trinkaus et al.

(10) Patent No.: US 10,966,880 B2
(45) Date of Patent: *Apr. 6, 2021

(54) METHODS AND TOOLING FOR MAKING THREE-DIMENSIONAL SUBSTRATES FOR ABSORBENT ARTICLES

(71) Applicant: The Procter & Gamble Company, Cincinnati, OH (US)

(72) Inventors: Jan Michael Trinkaus, Euskirchen (DE); Hans Adolf Jackels, Mechernich (DE); Gueltekin Erdem, Beijing (CN); Uwe Schneider, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/791,386

(22) Filed: Feb. 14, 2020

(65) Prior Publication Data

US 2020/0179186 A1 Jun. 11, 2020

Related U.S. Application Data

(63) Continuation of application No. 15/893,727, filed on Feb. 12, 2018, now Pat. No. 10,603,229.

(Continued)

(51) Int. Cl.
*A61F 13/511* (2006.01)
*A61F 13/512* (2006.01)
(Continued)

(52) U.S. Cl.
CPC .. *A61F 13/51104* (2013.01); *A61F 13/00995* (2013.01); *A61F 13/15203* (2013.01); *A61F 13/15577* (2013.01); *A61F 13/15642* (2013.01); *A61F 13/49* (2013.01); *A61F 13/5116* (2013.01); *A61F 13/5121* (2013.01);
(Continued)

(58) Field of Classification Search
CPC ............ A61F 13/51104; A61F 13/5121; A61F 13/5123; A61F 13/15577
See application file for complete search history.

(56) References Cited

U.S. PATENT DOCUMENTS 4,614,679 A 9/1986 Farrington, Jr. et al.
5,667,619 A 9/1997 Alikhan
(Continued)

FOREIGN PATENT DOCUMENTS

CN 1197538 C 4/2005
CN 202069775 U 12/2011
(Continued)

OTHER PUBLICATIONS

All Office Actions, U.S. Appl. No. 15/893,727.
(Continued)

*Primary Examiner* — Mark A Osele
*Assistant Examiner* — Christopher C Caillouet
(74) *Attorney, Agent, or Firm* — Christian M. Best

(57) ABSTRACT

Methods and tooling for making three-dimensional substrates and/or apertured substrates are provided. The three-dimensional substrates and/or apertured substrates may be used in absorbent articles, such as diapers and pants, for example. The methods and tooling may be used on an absorbent article manufacturing line.

19 Claims, 37 Drawing Sheets

Related U.S. Application Data

(60) Provisional application No. 62/574,237, filed on Oct. 19, 2017, provisional application No. 62/574,242, filed on Oct. 19, 2017, provisional application No. 62/574,240, filed on Oct. 19, 2017, provisional application No. 62/574,245, filed on Oct. 19, 2017, provisional application No. 62/458,173, filed on Feb. 13, 2017, provisional application No. 62/458,060, filed on Feb. 13, 2017, provisional application No. 62/458,051, filed on Feb. 13, 2017.

(51) Int. Cl.
| | | |
|---|---|---|
| *A61F 13/15* | (2006.01) | |
| *A61F 13/49* | (2006.01) | |
| *A61F 13/539* | (2006.01) | |
| *A61F 13/00* | (2006.01) | |
| *A61F 13/514* | (2006.01) | |
| *A61F 13/53* | (2006.01) | |

(52) U.S. Cl.
CPC .... *A61F 13/5123* (2013.01); *A61F 13/51121* (2013.01); *A61F 13/51476* (2013.01); *A61F 13/51484* (2013.01); *A61F 13/51496* (2013.01); *A61F 13/53* (2013.01); *A61F 13/539* (2013.01)

(56) References Cited

U.S. PATENT DOCUMENTS

| | | | |
|---|---|---|---|
| 6,274,218 | B1 | 8/2001 | Shimizu |
| 7,534,928 | B2 | 5/2009 | Sakamoto et al. |
| 7,569,264 | B2 | 8/2009 | Toyoshima et al. |
| 7,971,526 | B2 | 7/2011 | Blenke et al. |
| 8,221,370 | B2 | 7/2012 | Cohen et al. |
| 8,450,557 | B2 | 5/2013 | Nishitani et al. |
| 9,108,355 | B2 | 8/2015 | Kume et al. |
| 9,532,908 | B2 | 1/2017 | Wade et al. |
| 10,603,229 | B2 * | 3/2020 | Trinkaus .................. A61F 13/49 |
| 2001/0036786 | A1 | 11/2001 | Heden et al. |
| 2002/0016122 | A1 | 2/2002 | Curro et al. |
| 2003/0121380 | A1 | 7/2003 | Cowell et al. |
| 2003/0187418 | A1 | 10/2003 | Kudo et al. |
| 2006/0003657 | A1 | 1/2006 | Larson et al. |
| 2006/0144503 | A1 | 7/2006 | Carr |
| 2006/0243367 | A1 | 11/2006 | Engelhart et al. |
| 2008/0221543 | A1 | 9/2008 | Wilkes et al. |
| 2008/0260996 | A1 | 10/2008 | Heilman et al. |
| 2008/0294135 | A1 | 11/2008 | Hara et al. |
| 2012/0064298 | A1 | 3/2012 | Orr et al. |
| 2012/0238978 | A1 | 9/2012 | Weisman et al. |
| 2012/0276341 | A1 | 11/2012 | Lake et al. |
| 2014/0023822 | A1 | 1/2014 | Tai et al. |
| 2014/0080692 | A1 | 3/2014 | Lenser et al. |
| 2014/0296815 | A1 | 10/2014 | Takken et al. |
| 2014/0324009 | A1 | 10/2014 | Lee et al. |
| 2015/0164705 | A1 | 6/2015 | Thomas et al. |
| 2015/0290050 | A1 | 10/2015 | Wada |
| 2015/0351973 | A1 | 12/2015 | Tsujimoto et al. |
| 2016/0136003 | A1 | 5/2016 | Mullane et al. |
| 2016/0235590 | A1 | 8/2016 | Coe et al. |
| 2016/0235592 | A1 | 8/2016 | Coe et al. |
| 2016/0354254 | A1 | 12/2016 | Eimann et al. |
| 2017/0014281 | A1 | 1/2017 | Xie et al. |
| 2018/0000656 | A1 | 1/2018 | Roe et al. |
| 2018/0228667 | A1 | 8/2018 | Schneider et al. |

FOREIGN PATENT DOCUMENTS

| | | |
|---|---|---|
| CN | 202096358 U | 1/2012 |
| CN | 202515887 U | 11/2012 |
| CN | 202644115 U | 1/2013 |
| CN | 202982411 U | 6/2013 |
| CN | 204237074 U | 4/2015 |
| CN | 204798134 U | 11/2015 |
| CN | 103339309 B | 6/2016 |
| JP | H05228173 | 9/1993 |
| JP | 3748763 B | 2/2006 |
| JP | 2009153879 | 7/2009 |
| JP | 2010133071 | 6/2010 |
| JP | 2011132623 | 7/2011 |
| JP | 5021719 B | 9/2012 |
| JP | 5103100 B | 12/2012 |
| JP | 201425187 A | 2/2014 |
| JP | 5674454 B | 2/2015 |
| JP | 5674455 B | 2/2015 |
| JP | 5764323 B | 8/2015 |
| JP | 5858776 B | 2/2016 |
| JP | 5921866 B | 5/2016 |
| JP | 5985258 B | 9/2016 |
| JP | 2009153879 | 7/2019 |
| WO | WO2003015681 | 2/2003 |
| WO | WO2015098373 | 7/2015 |
| WO | WO2016040104 | 3/2016 |
| WO | WO2018020677 | 2/2018 |

OTHER PUBLICATIONS

All Office Actions, U.S. Appl. No. 15/893,730.
All Office Actions, U.S. Appl. No. 15/893,740.
All Office Actions, U.S. Appl. No. 15/893,735.
All Office Actions, U.S. Appl. No. 15/893,835.
International Search Report and Written Opinion, PCT/US2018/017794, dated May 17, 2018.
All Office Actions, U.S. Appl. No. 16/791,386.
All Office Actions, U.S. Appl. No. 16/208,810.
International Search Report and Written Opinion, PCT/US2018/064152, dated May 8, 2019.

* cited by examiner

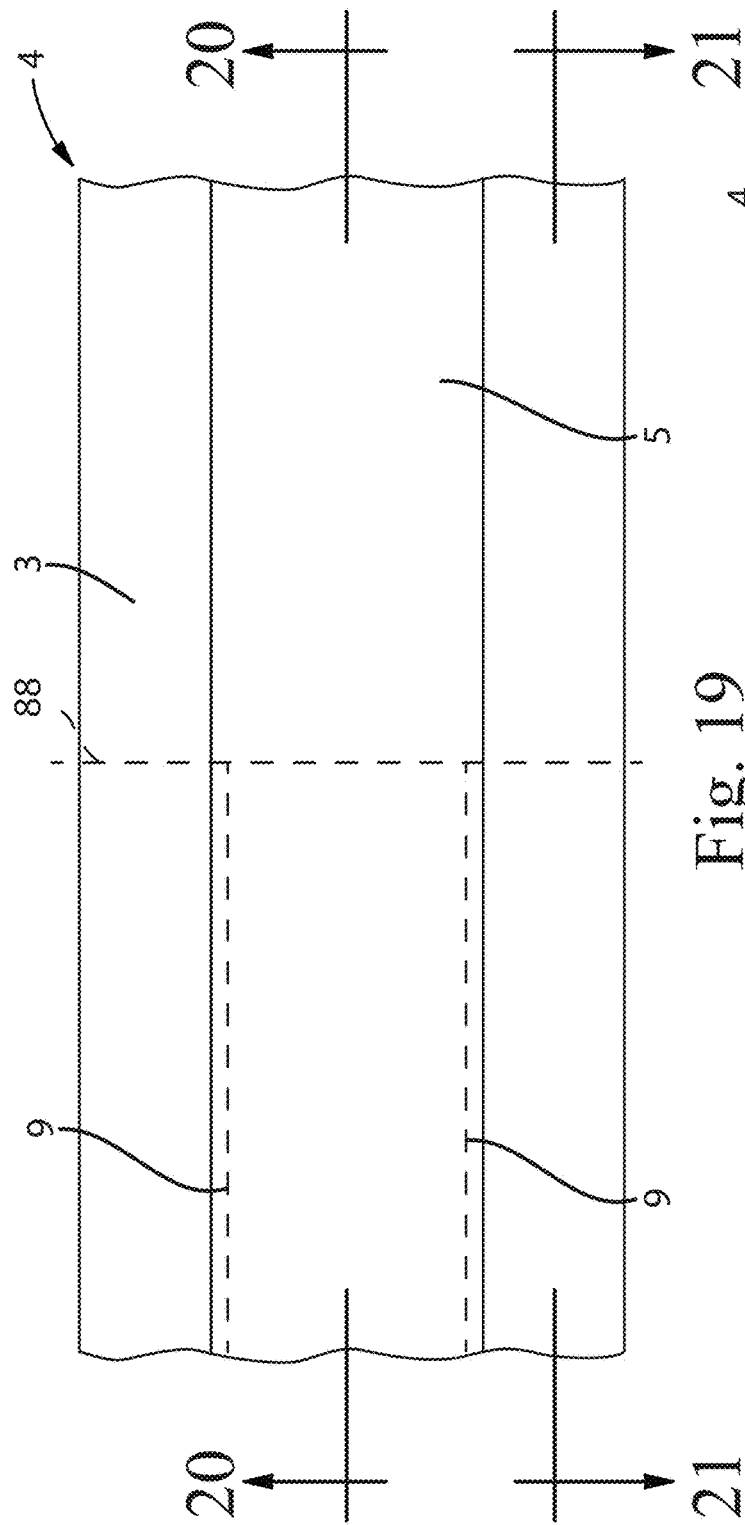
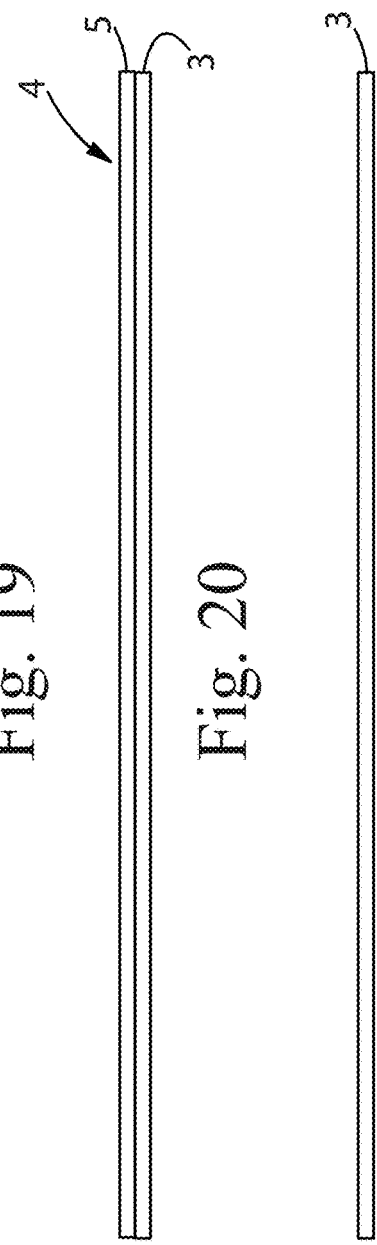
Fig. 19
Fig. 20
Fig. 21

METHODS AND TOOLING FOR MAKING THREE-DIMENSIONAL SUBSTRATES FOR ABSORBENT ARTICLES

CROSS REFERENCE TO RELATED APPLICATIONS

This application is a continuation of, and claims priority under 35 U.S.C. § 120 to, U.S. patent application Ser. No. 15/893,727, filed on Feb. 12, 2018, now U.S. Pat. No. 10,603,229, which claims the benefit, under 35 U.S.C. § 119(e), of U.S. Provisional Patent Application No. 62/458,051, filed on Feb. 13, 2017; U.S. Provisional Patent Application No. 62/574,237, filed on Oct. 19, 2017; U.S. Provisional Patent Application No. 62/458,060, filed on Feb. 13, 2017; U.S. Provisional Patent Application No. 62/574,240, filed on Oct. 19, 2017; U.S. Provisional Patent Application No. 62/458,173, filed on Feb. 13, 2017; U.S. Provisional Patent Application No. 62/574,242, filed on Oct. 19, 2017; and U.S. Provisional Patent Application No. 62/574,245, filed on Oct. 19, 2017, which are all herein incorporated by reference in their entirety.

FIELD

The present disclosure is directed to methods and tooling for making three-dimensional substrates, and is more particularly related to methods and tooling for making three-dimensional substrates for absorbent articles.

BACKGROUND

Three-dimensional substrates have a variety of uses in various industries. One of the industries that has interest in three-dimensional substrates is the absorbent article industry. The absorbent article industry manufactures products such as diapers, pants, sanitary napkins, tampons, and adult incontinence pants, diapers, and products, for example. These "absorbent articles" may desirably comprise one or more three-dimensional substrates as topsheets, acquisition layers, distribution layers, outer cover materials, and/or other components, for example. Three-dimensional means substrates that have three-dimensional elements more than a standard generally planar material. As an example, three-dimensional elements may extend 0.5 mm to 5 mm or 1 mm to 5 mm, for example, from a planar surface of the substrates. Three-dimensional substrates used in absorbent articles are typically manufactured at a first location and then shipped to a second, different location for incorporation into absorbent articles. The first location is typically a three-dimensional substrate manufacturer, or a nonwoven or film manufacturer, and the second, different location is typically an absorbent article manufacturer. A first issue that arises in these situations is the three-dimensional substrates need to be tightly wound at the first location and then shipped to a second, different location. This typically reduces the three-dimensionality of the substrates due to their lack of ability to withstand compression and tensioning caused by the winding. A second issue that arises in these situations is the substrates need to be unwound and fed into absorbent article manufacturing lines at the second, different location. This typically further reduces the three-dimensionality of the substrates owing to their lack of ability to withstand compression and tensioning caused by the unwinding. Finally, compact packaging, as often used for absorbent articles, reduces three-dimensionality further. What is needed are reliable methods and tooling for producing three-dimensional substrates on an absorbent article manufacturing line that reduce three-dimensional feature compression and distortion.

SUMMARY

The present disclosure provides methods and tooling for producing three-dimensional substrates on an absorbent article manufacturing line. By creating the three-dimensional substrates on the absorbent article manufacturing line, winding, unwinding, and shipping are eliminated. Further, the methods and tooling of the present disclosure provide the three-dimensional substrates the ability to at least reduce three-dimensional feature compression, even during compression packaging of the absorbent articles. This compression resistance may be accomplished by providing compressed regions or densified areas in at least some of the three-dimensional elements of the three-dimensional substrates. The compressed regions or densified areas may be formed around aperture perimeters, or portions of aperture perimeters, to stabilize the apertures at line speed.

BRIEF DESCRIPTION OF THE DRAWINGS

While the specification concludes with claims particularly pointing out and distinctly claiming the subject matter which is regarded as forming the present invention, it is believed that the present disclosure will be better understood from the following description which is taken in conjunction with the accompanying drawings in which the designations are used to designate substantially identical elements and in which:

FIG. 19 is a top view of an example precursor substrate that may be conveyed through a nip formed between first and second rolls of the present disclosure;

FIG. 20 is a cross-sectional view of the precursor substrate taken about line 20-20 of FIG. 19;

FIG. 21 is a cross-sectional view of the precursor substrate taken about line 21-21 of FIG. 19;

DETAILED DESCRIPTION

Various non-limiting forms of the present disclosure will now be described to provide an overall understanding of the principles of the structure, function, manufacture, and use of the methods and tooling for making three-dimensional substrates for absorbent articles disclosed herein. One or more examples of these non-limiting forms are illustrated in the accompanying drawings. Those of ordinary skill in the art will understand that the methods and tooling for making three-dimensional substrates for absorbent articles specifically described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

Figure 1:
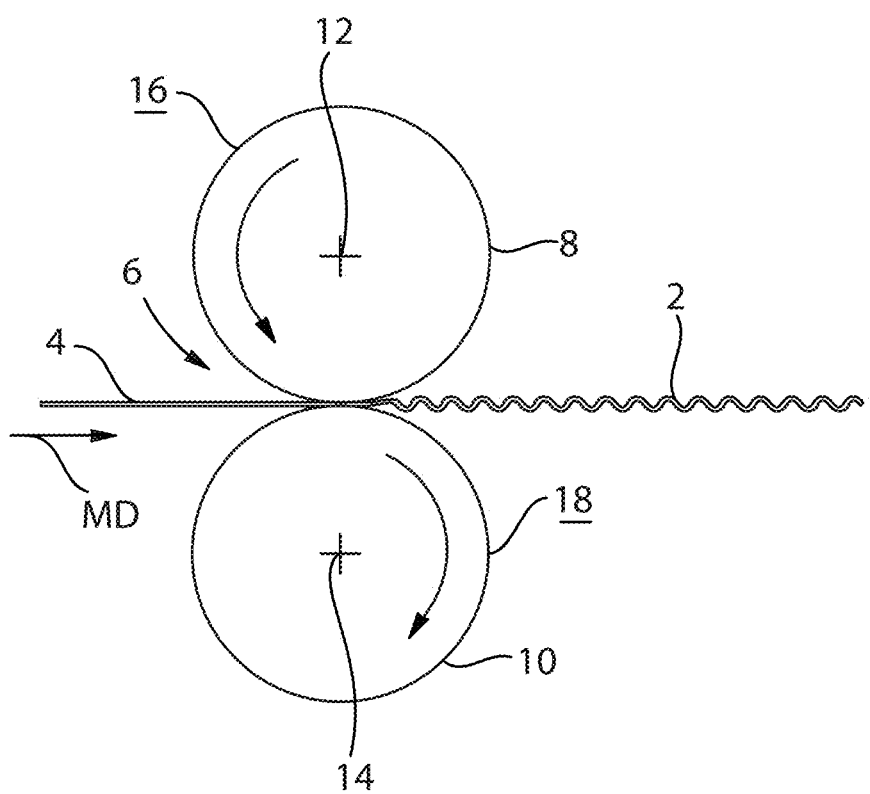
FIG. 1 is a view of a pair of rolls having a substrate conveyed therebetween.

The present disclosure is directed, in part, to methods and tooling for making three-dimensional substrates on an absorbent article manufacturing line. The three-dimensional substrates may be apertured. Referring to FIG. 1, the three-dimensional substrates, or three-dimensional apertured substrates 2, may be created by conveying a precursor substrate 4 through a nip 6 formed between a first roll 8 and a second roll 10. At least portions of the first roll 8 may be intermeshing engaged with at least portions of the second roll 10. Portions of the first and second rolls that are not in intermeshing contact may be in rolling contact or not in contact at all. Details of the first and second rolls 8, 10 will be illustrated in later figures. The precursor substrate 4, the first roll 8, the second roll 10, and/or the three-dimensional substrate or three-dimensional apertured substrate 2 may be heated to promote better retention of three-dimensional elements in the substrate 2 and allow easier formation of three-dimensional elements and apertures.

The precursor substrate 4 may have a thermoplastic component (e.g., one or more films and/or one or more nonwoven materials). The precursor substrate 4 may have any suitable number of layers, such as one, two, or three, for example. Any or all of the layers may comprise one or more nonwoven materials (or nonwoven fibers), films, coform materials, cellulosic materials (or cellulosic fibers), cotton materials (or cotton fibers), natural materials (or natural fibers), or combinations thereof. As an example, a precursor substrate may have two or more layers of nonwoven materials, one or more layers of films and one or more layers of nonwoven materials, and/or two or more layers of films. The various layers may have the same size, shape, density, basis weight, and composition or may have different sizes, shapes, densities, basis weights, and compositions as will be discussed in further detail below.

Referring again to FIG. 1, the first and second rolls 8 and 10 may be configured to create only three-dimensional elements in the precursor substrate 4 or may be configured to create three-dimensional elements and apertures in the precursor substrate 4 to form a three-dimensional, apertured substrate 2. The first roll 8 may rotate about a first rotational axis 12 in the direction indicated by the arrow on the first roll 8 and the second roll 10 may rotate about a second rotational axis 14 in the direction indicated by the arrow on the second roll 10. In other instances, the first roll 8 may rotate in the opposition direction as the arrow on the first roll 8 and the second roll 10 may rotate in the opposite direction as the arrow on the second roll 10, for example. The first roll 8 may comprise a first radial outer surface 16 and the second roll 10 may comprise a second radial outer surface 18. The first rotational axis 12 and the second rotational axis 14 may be positioned generally parallel to each other to form a nip 6 between the first and second rolls 8, 10. The precursor substrate 4 may be conveyed in a machine direction (arrow MD) on an absorbent article manufacturing line through the nip 6.

Figure 2:
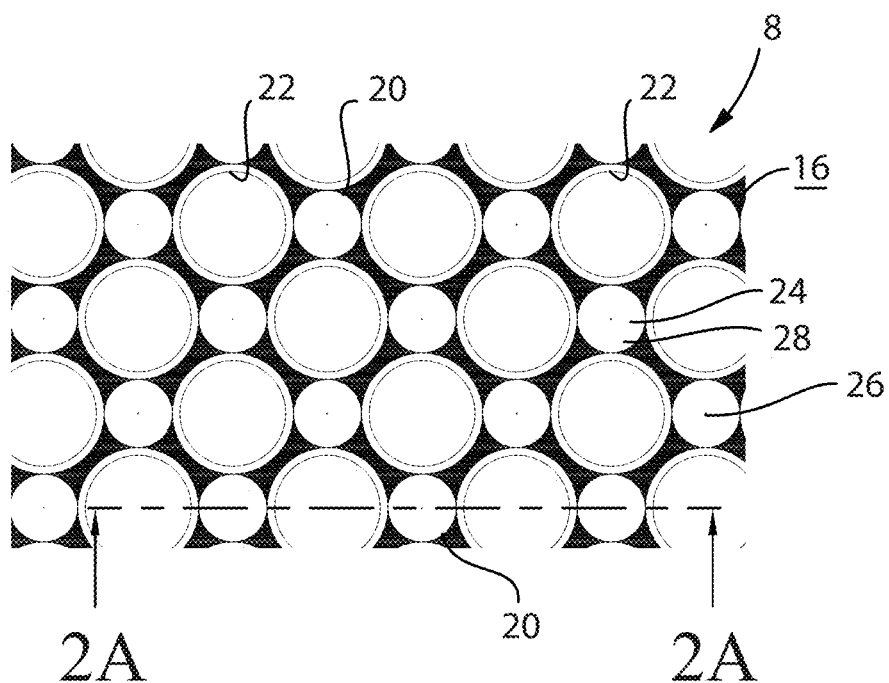
FIG. 2 is a top view of an example portion of a first roll of the pair of rolls of FIG. 1.
Figure 2A:
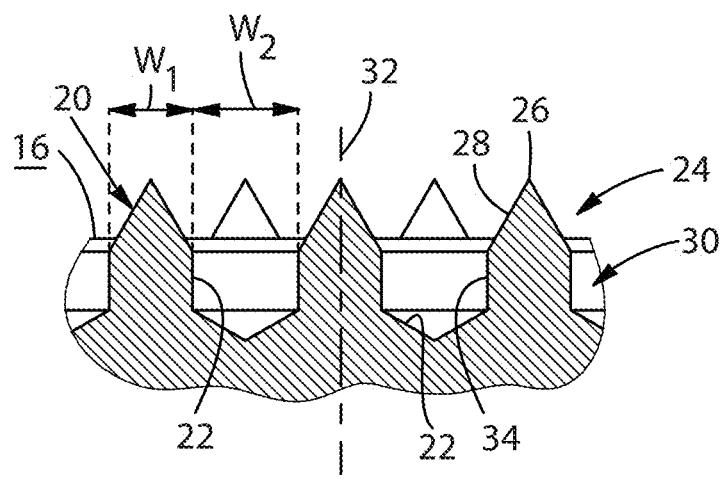
FIG. 2A is a cross-sectional view of the first roll taken about line 2A-2A of FIG. 2.

FIG. 2 is a front view of a portion of an example of the first roll 8. FIG. 2A is a cross-sectional view of FIG. 2 taken about line 2A-2A. The first roll 8 may comprise a first plurality of projections 20 extending at least partially outwardly from the first radial outer surface 16. The first plurality of projections 20 may be configured to form, or at least partially form apertures in the precursor substrate 4. In some instances, distal ends of the projections 20 may be rounded to merely form three-dimensional elements in the precursor substrate 4 instead of apertures. The first roll 8 may also comprise a first plurality of recesses 22 defined in the first radial outer surface 16. At least some of, most of, or all of the first plurality of projections 20 may comprise first distal portions 24 comprising elongated aperturing structures. First distal ends 26 of the first distal portions 24 may form a point. The term "point" as used herein may be at least partially rounded off, but still capable of puncturing a precursor substrate. The term "point" also includes a configuration where pins extend from the distal ends, wherein the pins create the apertures. The first distal portions 24 may comprise one or more side walls 28. At least some of, most of, or all of the first plurality of projections 20 may each comprise a first base 30. The first plurality of projections 20 may comprise a central longitudinal axis 32 that intersects the point or first distal end 26. The base 30 may comprise side walls 34 that may extend parallel to, or substantially parallel to, the first central longitudinal axis 32. In other instances, the side walls 34 may extend within +/−25 degrees of the first central longitudinal axis 32. The side walls 34, in some instances, may also be arcuate or have arcuate portions.

Still referring to FIGS. 2 and 2A, the first distal portions 24 may form cones or conical structures. In such instances, the first distal portions 24 may have a single side wall 28 that surrounds the first central longitudinal axis 32. In other instances, the first distal portions 24 may form other polygonal shapes where two or more side walls 28 are formed. As an example, the first distal portions 24 may form tetrahedron structures with three separate side walls. In either instance, the side wall or side walls 28 may not be fully continuous around the first central longitudinal axis 32 as will be explained in further detail below. The side wall or walls 28, whether continuous or discontinuous, may have a first angle in the range of about 5 degrees to about 50 degrees, about 10 degrees to about 30 degrees, about 15 degrees to about 25 degrees, about 18 degrees, about 20 degrees to about 80 degrees, about 30 degrees to about 70 degrees, about 35 degrees to about 65 degrees, about 40 degrees to about 60 degrees, about 40 degrees to about 55 degrees, or about 40 degrees to about 50 degrees, relative to the first central longitudinal axis 32, specially reciting all 0.1 degree increments within the specified ranges and all ranges formed therein or thereby. Referring to FIG. 2, at least some of the projections of first plurality of projections 20 may be surrounded by four recesses of the first plurality of recesses 22, for example. Again referring to FIG. 2, at least some of the recesses of the first plurality of recesses 22 may be surrounded by four projections of the first plurality of projections 20, for example.

Referring to FIG. 2A, at least some of, or all of, the bases 30 of the first plurality of projections 20 may have a first width, W1, taken in a direction generally parallel to the first rotational axis 12 (or perpendicular to the first central longitudinal axis 32). At least some of the recesses 22 in areas adjacent to the bases 30 may have a second width, W2, taken in a direction generally parallel to the first rotational axis 12. The first width, W1, may be the same as, different than, smaller than, or greater than the second width, W2.

Figure 3:
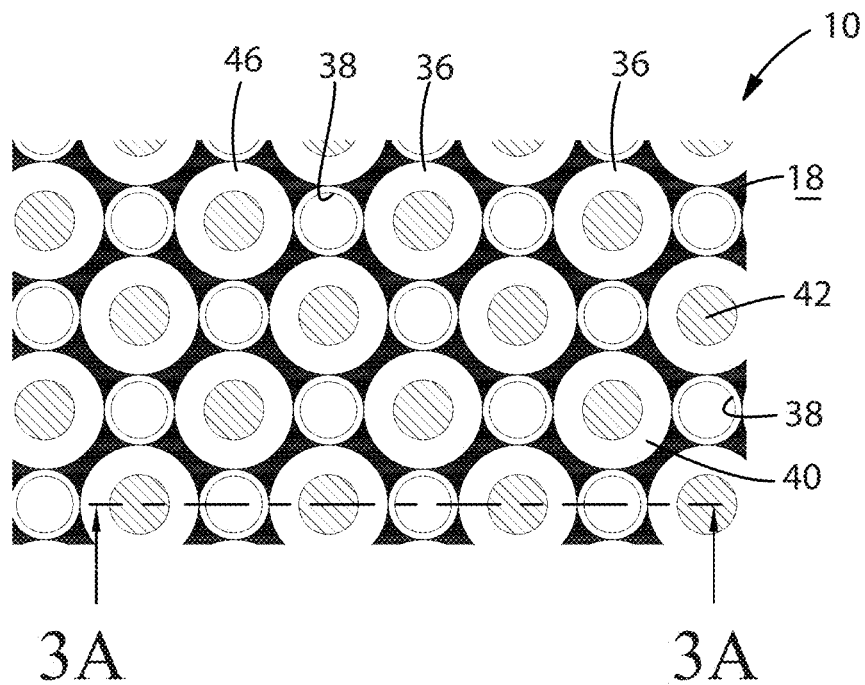
FIG. 3 is a top view of an example portion of a second roll of the pair of rolls of FIG. 1.
Figure 3A:
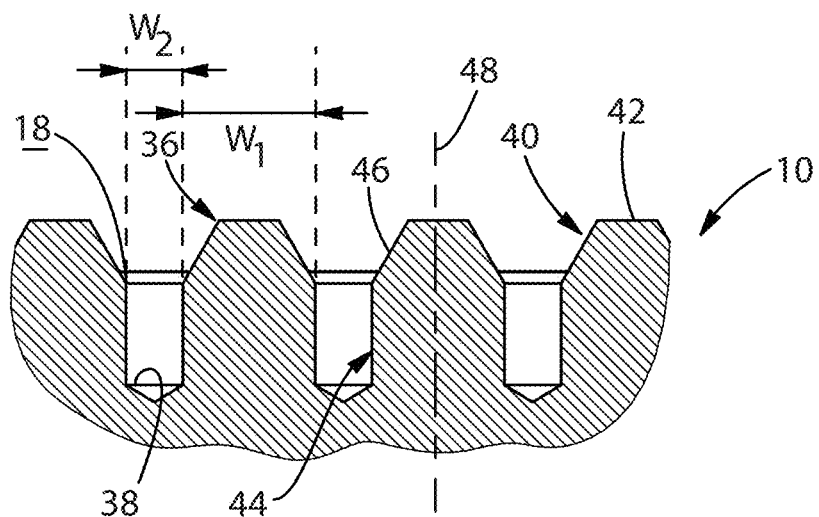
FIG. 3A is a cross-sectional view of the second roll taken about line 3A-3A of FIG. 3.

FIG. 3 is a front view of a portion of an example of the second roll 10. FIG. 3A is a cross-sectional view of FIG. 3 taken about line 3A-3A. The second roll 10 may comprise a second plurality of projections 36 extending at least partially outwardly from the second radial outer surface 18. The second plurality of projections 36 are configured to form three-dimensional elements in the precursor substrate 4. The second plurality of projections 36 have a second plurality of recesses 38 defined in the second radial outer surface 18. At least some of, most of, or all of the second plurality of projections 36 comprise second distal portions 40 and second distal ends 42. The second plurality of projections 36 comprise bases 44. At least some of, most of, or all of the second plurality of projections 36 each comprise shoulders 46 positioned intermediate the bases 44 and the second distal ends 42. The second plurality of projections 36 each comprise a central longitudinal axis 48 extending in a direction generally perpendicular to the second rotation axis 14. The shoulders 46 may have a second angle relative to the second central longitudinal axis 48 in the range of about 2 degrees to about 40 degrees, about 3 degrees to about 30 degrees, about 5 degrees to about 20 degrees, about 3 degrees to about 15 degrees, about 10 degrees, about 20 degrees to about 80 degrees, about 30 degrees to about 70 degrees, about 35 degrees to about 65 degrees, about 40 degrees to about 60 degrees, about 40 degrees to about 55 degrees, or about 40 degrees to about 50 degrees, relative to the second central longitudinal axis 48, specially reciting all 0.1 degree increments within the specified ranges and all ranges formed therein or thereby. The first angle of the first distal portions 24 may be the same as or different than the second angle of the shoulders 46. As an example, the first angle may be within about +/−0.01 degrees to about 15 degrees, or within about +/−0.01 degrees to about 10 degrees, of the second angle, specifically including all 0.001 degree increments within the specified ranges and all ranges formed therein or thereby. As further examples, the first angle may be with +/−15, 14, 13, 12, 11, 10, 9, 8, 6, 5, 4, 3, 2, 1.5, 1, 0.75, 0.5, 0.25, or 0.1 degrees of the second angle. As yet another example, the first angle may be substantially the same as (e.g., +/−0.5 degrees), or the same as, the second angle. The purpose of having the first and second angles the same, substantially the same, or relatively close to each other is to create a compressed region or densified area at least partially, or fully, surrounding a portion of three-dimensional elements (or surrounding or partially surrounding the apertures) in the precursor substrate 4. These compressed regions or densified areas help resist compression (such as from packaging) and help maintain the three-dimensional elements. The compressed regions may be formed on portions of the three-dimensional elements and/or may at least partially surround perimeters of the apertures to stabilize the three-dimensional elements and/or the apertures when made at line speed. The compressed regions or densified areas are not merely primary fiber bonds used in the formation of a nonwoven substrate (i.e., bonds used to hold the fibers together).

Referring to FIG. 3, at least some of the projections of second plurality of projections 36 may be surrounded by four recesses of the second plurality of recesses 38. Again referring to FIG. 3, at least some of the recesses of the second plurality of recesses 38 may be surrounded by four projections of the second plurality of projections 36.

Referring to FIG. 3A, at least some of, or all of, the bases 44 of the second plurality of projections 36 may have a first width, W3, in a direction generally parallel to the second rotational axis 14. At least some of the recesses 38 in areas adjacent to the bases 44 may have a second width, W4, in a direction generally parallel to the second rotational axis 14. The first width, W1, may be the same as, different than, smaller than, or greater than the second width, W2.

Figure 4:
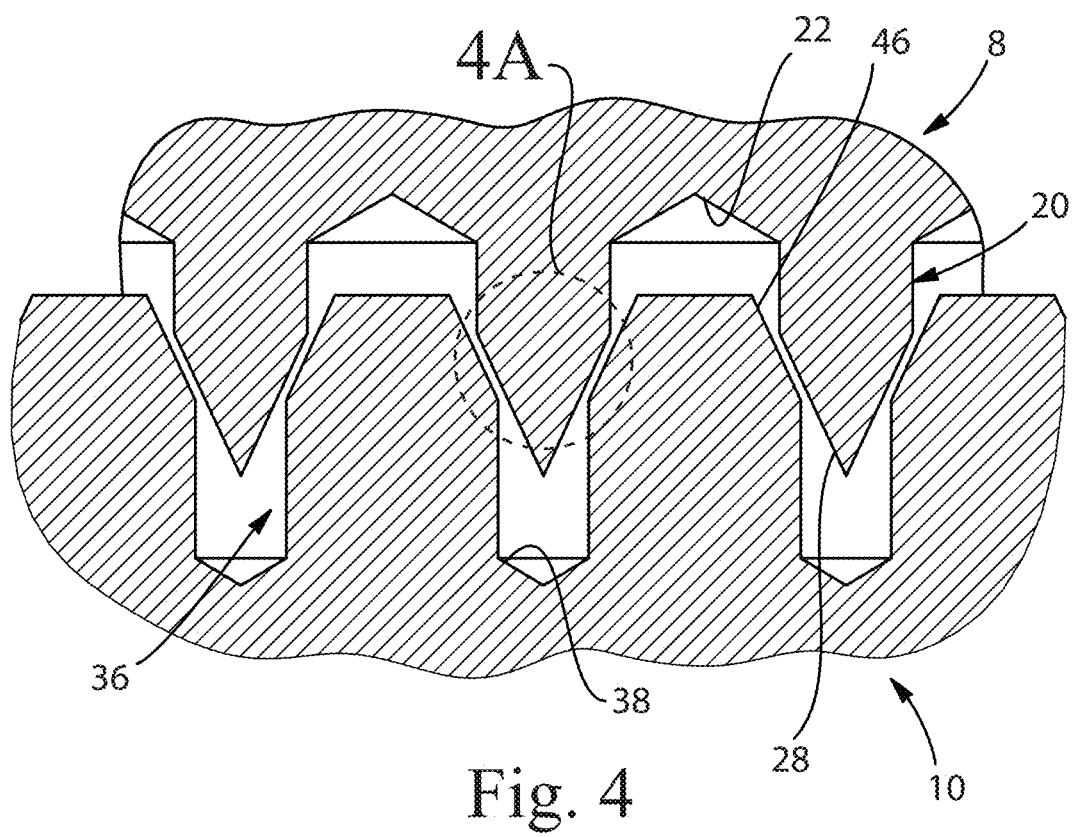
FIG. 4 is a simplified schematic cross-sectional illustration of the portion of the first roll of FIG. 2A intermeshed with the portion of the second roll of FIG. 3A.

FIG. 4 is a simplified schematic cross-sectional illustration of the portion of the first roll 8 of FIG. 2A intermeshed with the portion of the second roll 10 of FIG. 3A. The remainder of the outer surface of the first roll 8 having the first plurality of projections 20 and the first plurality of recesses 22 and the remainder of the second roll 10 having the second plurality of projections 36 and the second plurality of recesses 38 will, in most instances, intermesh in the same fashion, if desired. In some instances, it may be desirable to only create three-dimensional elements and apertures in a central longitudinal strip, as will be discussed in more detail below. The precursor substrate 4 is not illustrated in FIG. 4 for clarity in illustration of the tooling, but would be present in the gap between the two rolls 8, 10. In FIG. 4, portions of the first plurality of projections 20 of the first roll 8 are intermeshed with portions of the second plurality of recesses 38 in the second roll 10. Also, portions of the second plurality of projections 36 of the second roll 10 are intermeshed with portions of the first plurality of recesses 22 of the first roll 8. In such a fashion, portions of one or more side walls 28 of the first distal portions 24 are brought into close proximity to portions of the shoulders 46 of the second distal portions 40. The side walls 28 and the shoulders 46 together may apply a force to the precursor substrate 4 to compress the precursor substrate 4 therebetween. When the precursor substrate 4 is positioned in the nip between the first roll 8 and the second roll 8, the shoulders 46 and portions of the one or more side walls 28 may be used to create compressed regions or densified areas in the precursor substrate 4. The compressed regions or densified areas in the substrate may aid in resisting compression of three-dimensional elements. The compression may be classified as reversible elastic deformation of the precursor substrate 4 (e.g., a nonwoven material). Compression means squeezing air out of a lofty precursor substrate and causing straightening and/or nesting of the fibers of the precursor substrate. Compression does not mean causing, for example, polymer in a nonwoven material to begin flowing to fill the air voids and then solidifying (known as non-reversible elastic deformation). Non-reversible elastic deformation may create rigid areas in the precursor substrate, thereby reducing the precursor substrates' softness. Thus, reversible elastic deformation is more desirable than non-reversible elastic deformation in that it provides better softness while still providing resistance to compression of the three-dimensional elements. Thus, a gap, G, is provided between the side walls 28 and the shoulders 46 to only allow for compression of the precursor substrate therebetween without causing it to melt and solidify.

Figure 4A:
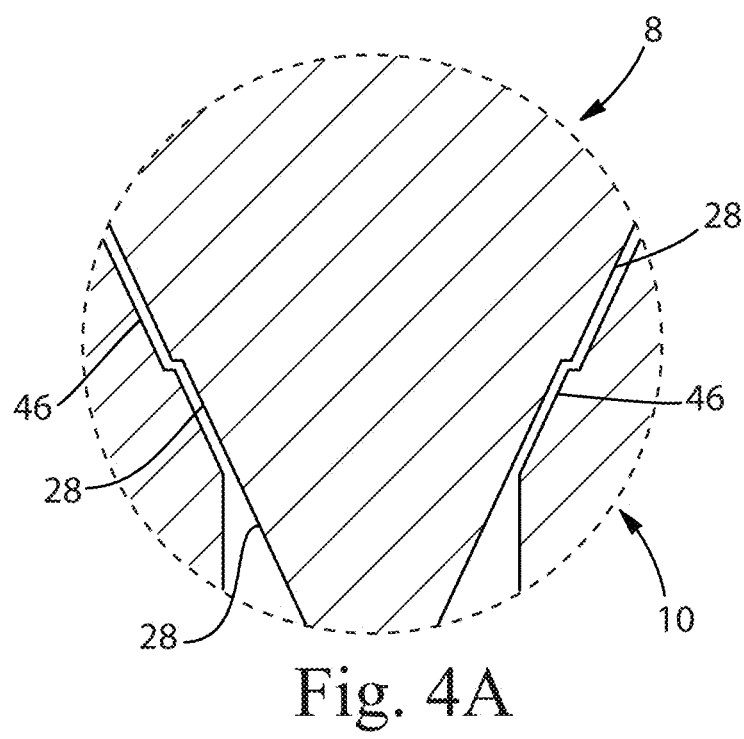
FIG. 4A is an exploded view of region 4A in FIG. 4.

FIG. 4A is an exploded view of region 4A of FIG. 4. FIG. 4A illustrates an example, optional configuration for the shoulders 46 and the side walls 28, wherein the shoulders 46 and the side walls 28 each have two off-set surfaces. Any of the shoulders 46 and the side walls 28 disclosed herein may have such off-set surfaces. In other instances, the shoulders 46 and the side walls 28 may not have two off-set surfaces.

The first plurality of projections 20 may not fully engage the second plurality of the recesses 38 and the second plurality of projections 36 may not fully engage the first plurality of the recesses 22. As stated above, the first plurality of projections 20, namely the points and the first distal portions 24, in combination with the second plurality of recesses 38, are used to form apertures in the precursor substrate 4. The second plurality of projections 36, namely the second distal ends 42 and the second distal portions 40, in combination with the first plurality of recesses 22 are used to form three-dimensional elements in the precursor substrate 4. The compressed regions may be formed in the three-dimensional elements to aid the three-dimensional elements to resist compression, such as compression caused by packaging.

Figure 5:
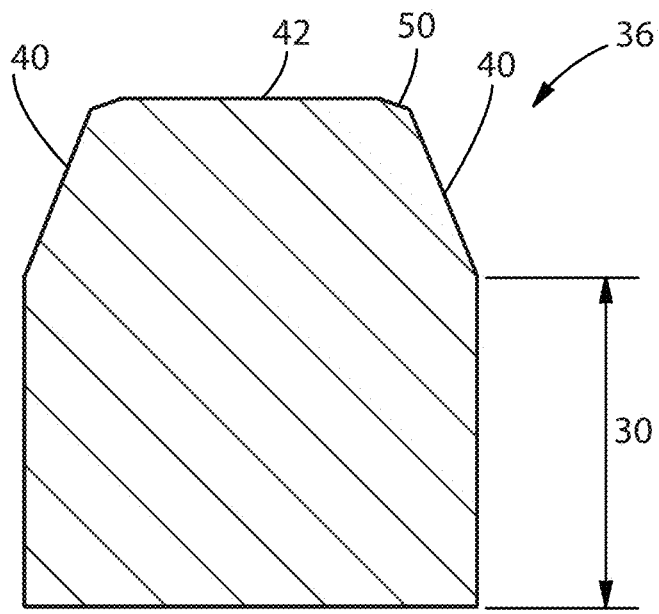
FIG. 5 is a cross-sectional view of a portion of an example projection of the second roll.
Figure 6:
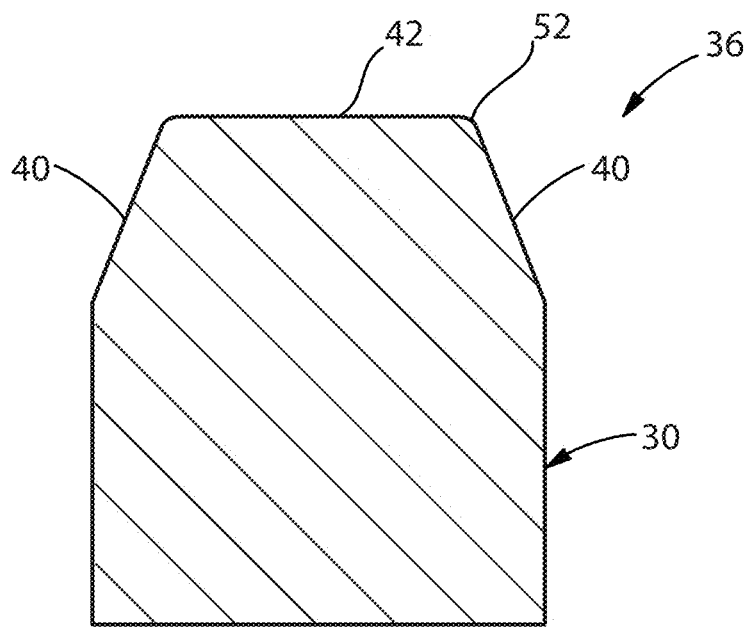
FIG. 6 is another cross-sectional view of a portion of an example projection of the second roll.

Referring to FIG. 5, at least some of the second plurality of projections 36 may have beveled portions 50 intermediate the second distal ends 42 and the second distal portions 40. This prevents, or at least inhibits, the precursor substrate 4 from contacting a sharp corner and tearing or creating a sharp edge in the precursor substrate 4. Referring to FIG. 6, at least some of the second plurality of projections 36 may have rounded corners 52 intermediate the second distal ends 42 and the second distal portions 40. This prevents, or at least inhibits, the precursor substrate 4 from contacting a sharp corner and tearing or creating a sharp edge in the precursor substrate 4.

Figure 7A:
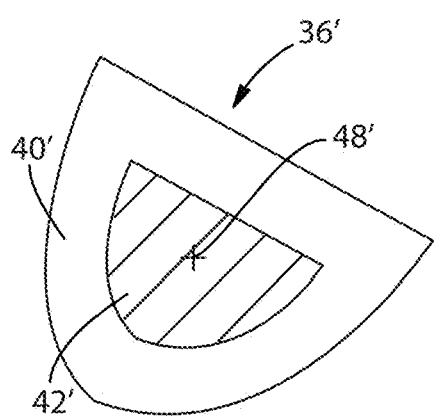
FIGS. 7A-7G are example top views of portions of distal ends of projections of the second roll.
Figure 7B:
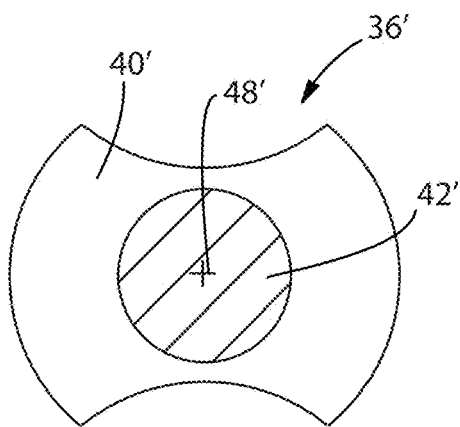
Figure 7C:
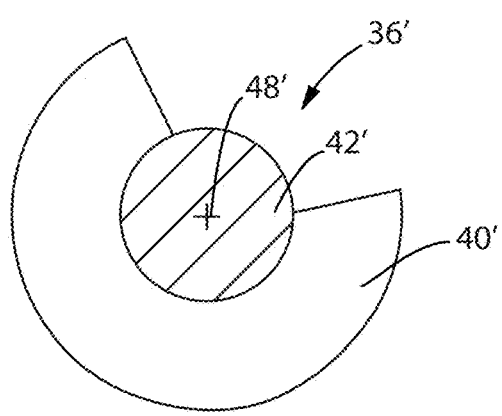
Figure 7D:
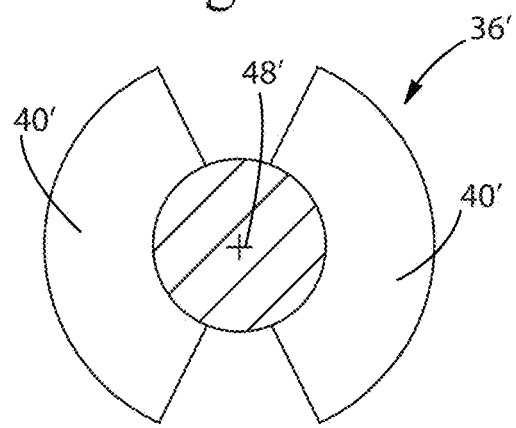
Figure 7E:
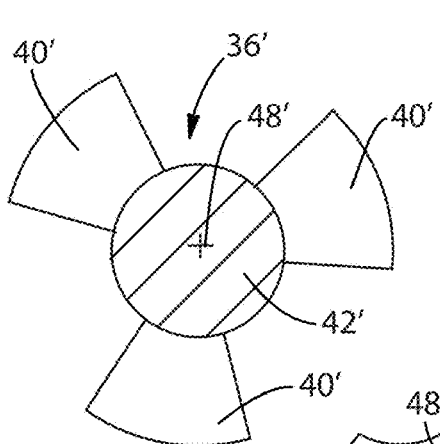
Figure 7F:
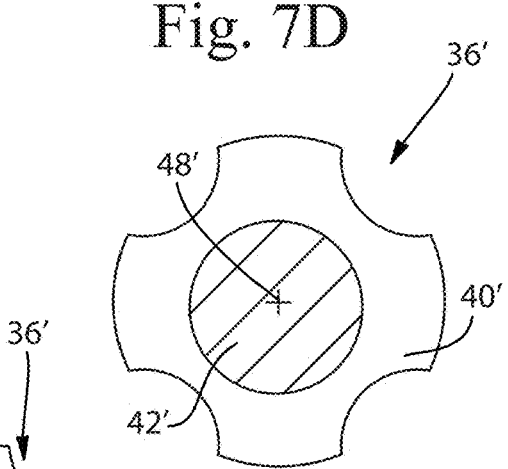
Figure 7G:
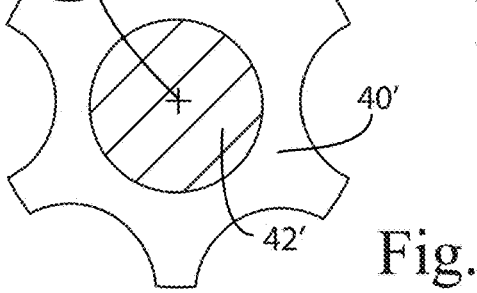
Figures 8A, 8B:
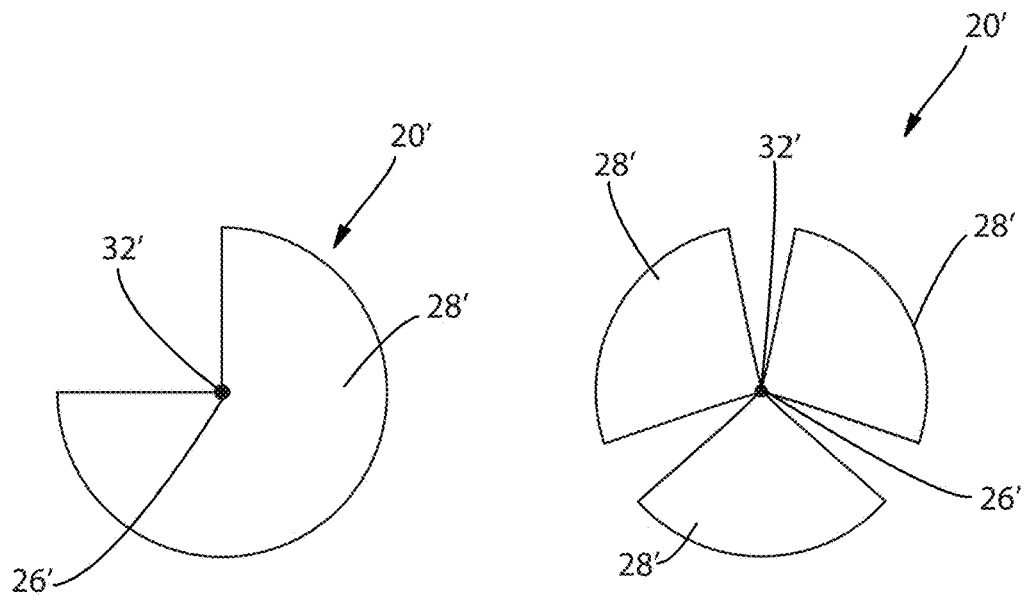
FIGS. 8A-8F are example top views of portions of projections of the first roll.
Figures 8C, 8D:
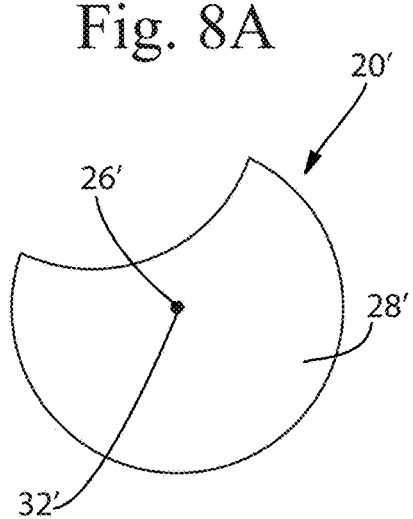
Figures 8E, 8F:
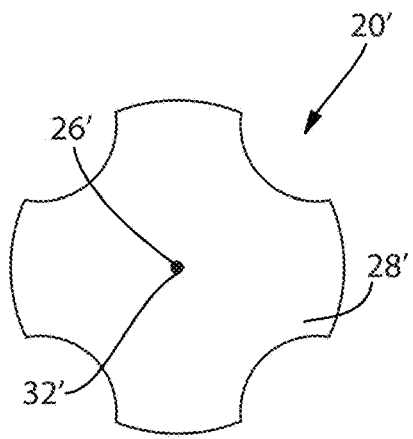

FIGS. 7A-7G are top view schematic illustrations of examples of different configurations of the second plurality of projections 36'. In such examples, the second distal portions 40' may not be the same shape as the shape of the second distal ends 42' (see e.g., FIGS. 7B-7G). In another example, the second distal portion 40' may be the same or a similar shape as the shape of the second distal ends (see e.g., FIG. 7A). Referring to FIGS. 7C-7E, the second distal portions 40' may not fully surround the second central longitudinal axes 48' of the second plurality of projections 36'. In such an instance, a compressed region or densified area in the substrate 2 may not fully surround a three-dimensional feature. Referring to FIGS. 7E and 7G, the second distal portions 40' may fully surround the second central longitudinal axes 48' of the second plurality of projections 36'. In such an instance, a compressed region or densified area in the substrate 2 may fully surround a three-dimensional feature.

FIGS. 8A-8F are top view schematic illustrations of examples of different configurations of the first plurality of projections 20'. The side walls 28' may fully surround the first central longitudinal axis 32' (see e.g., FIGS. 8C, 8E and 8F). In other instances, the side walls 28' may not fully surround the first central longitudinal axis 32' (see e.g., FIGS. 8A, 8B, and 8D). In some examples, the configuration of the side walls of the first plurality of projections 20 may or may not match the configuration of the second distal portions of the second plurality of projections.

Figure 9:
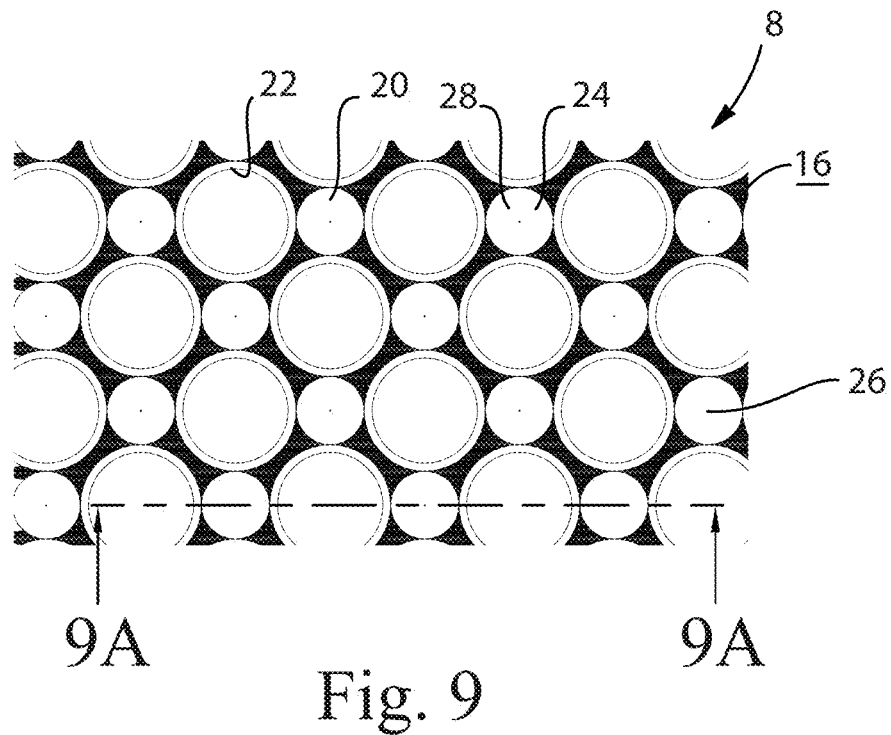
FIG. 9 is a top view of an example portion of a first roll of the pair of rolls of FIG. 1.
Figure 9A:
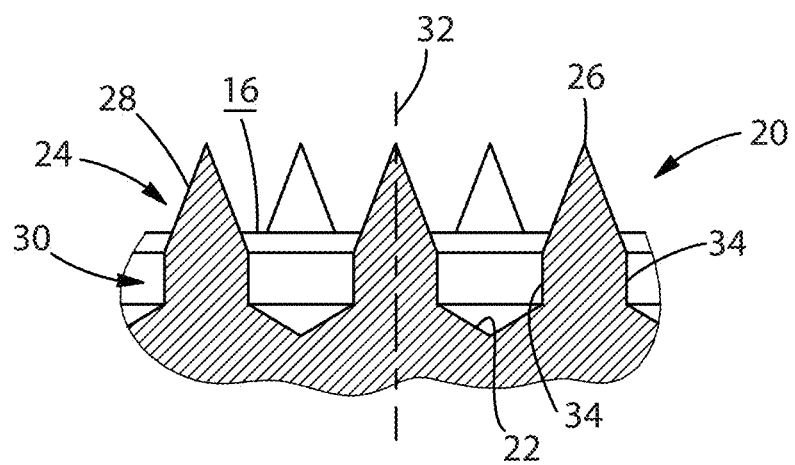
FIG. 9A is a cross-sectional view of the first roll taken about line 9A-9A of FIG. 9.
Figure 10:
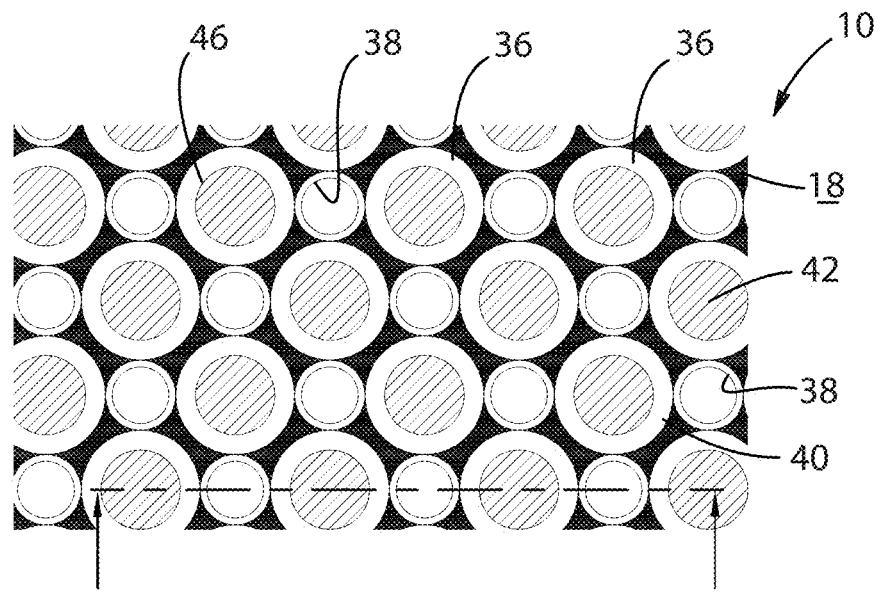
FIG. 10 is a top view of an example portion of a second roll of the pair of rolls of FIG. 1.
Figure 10A:
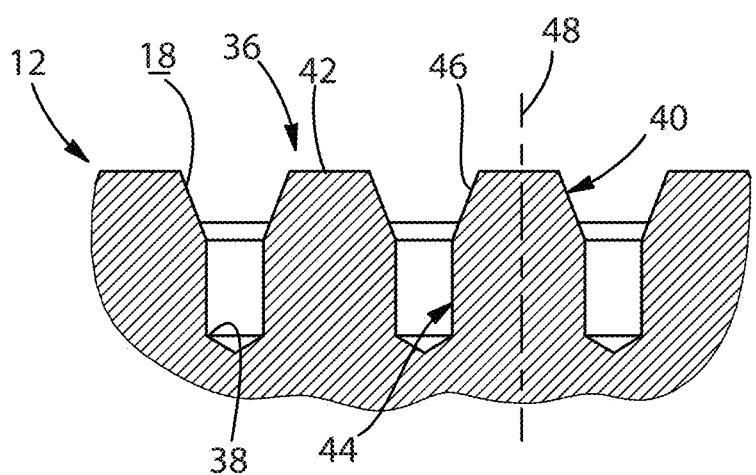
FIG. 10A is a cross-sectional view of the second roll taken about line 10A-10A of FIG. 10.
Figure 11:
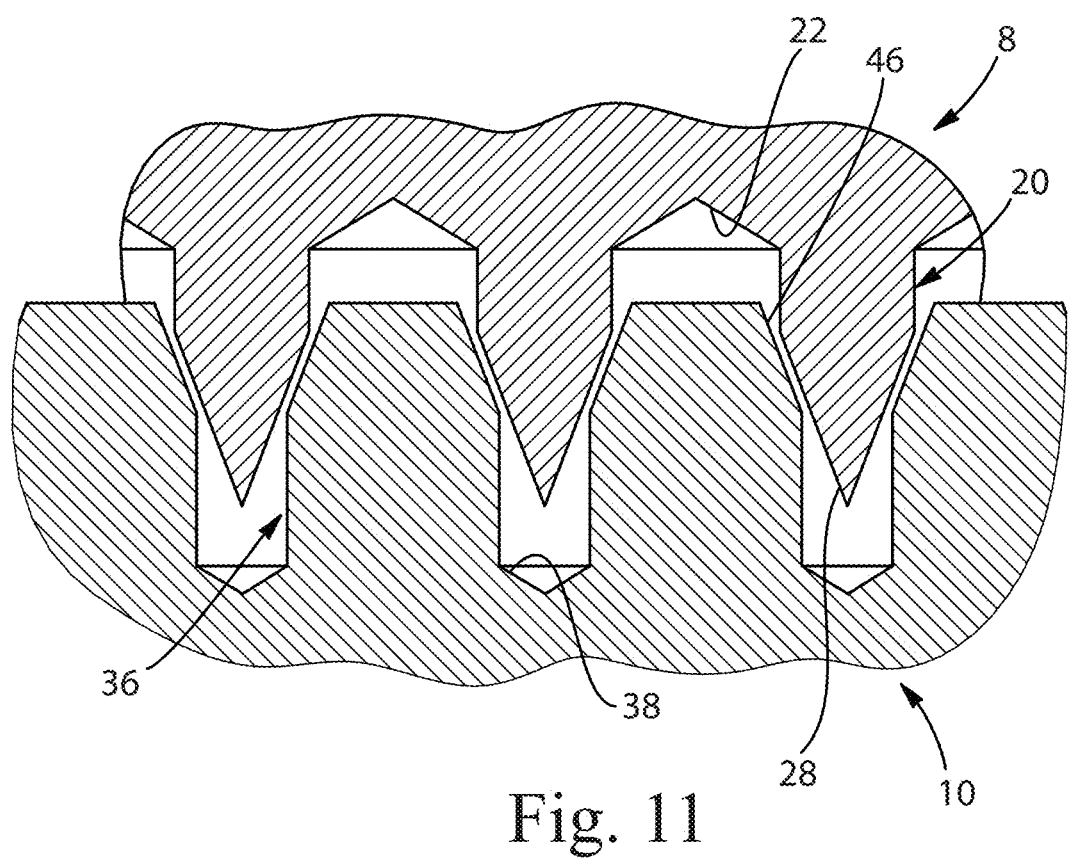
FIG. 11 is a simplified schematic cross-sectional illustration of the portion of the first roll of FIG. 9A intermeshed with the portion of the second roll of FIG. 10A.
Figure 12:
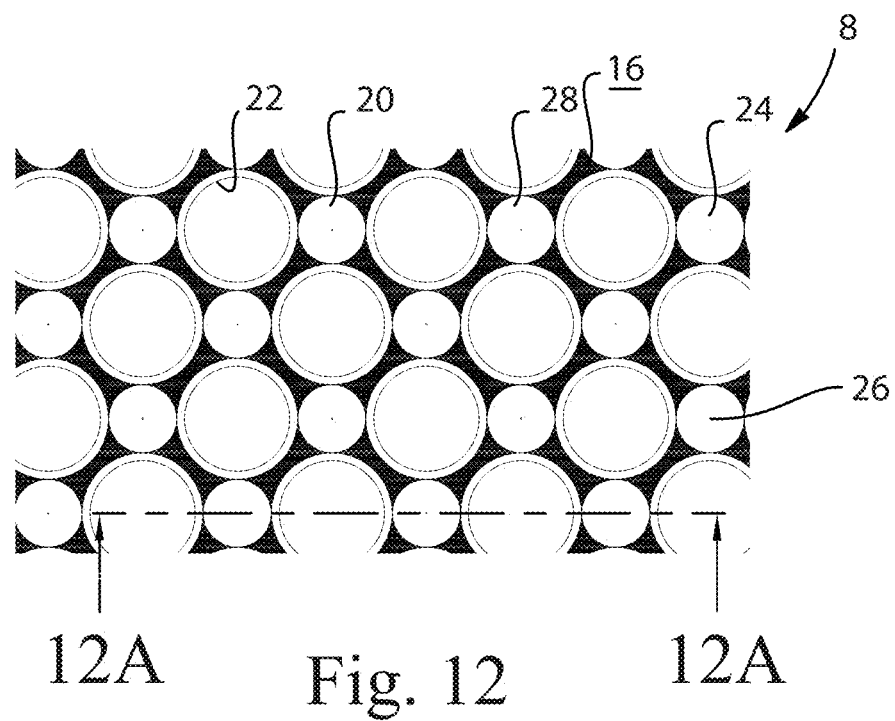
FIG. 12 is a top view of an example portion of a first roll of the pair of rolls of FIG. 1.
Figure 12A:
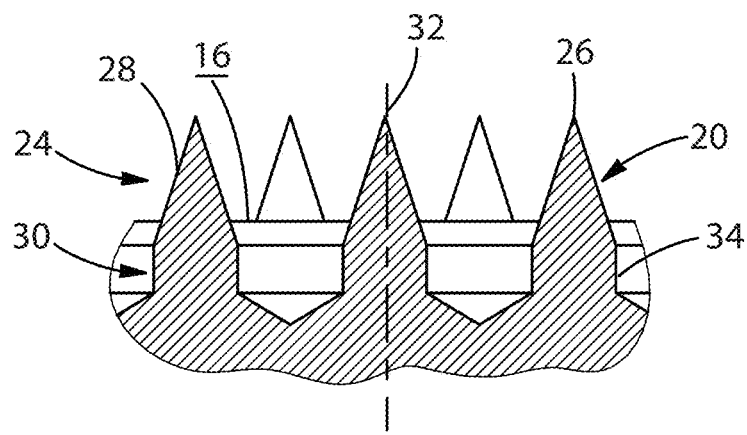
FIG. 12A is a cross-sectional view of the first roll taken about line 12A-12A of FIG. 12.
Figure 13:
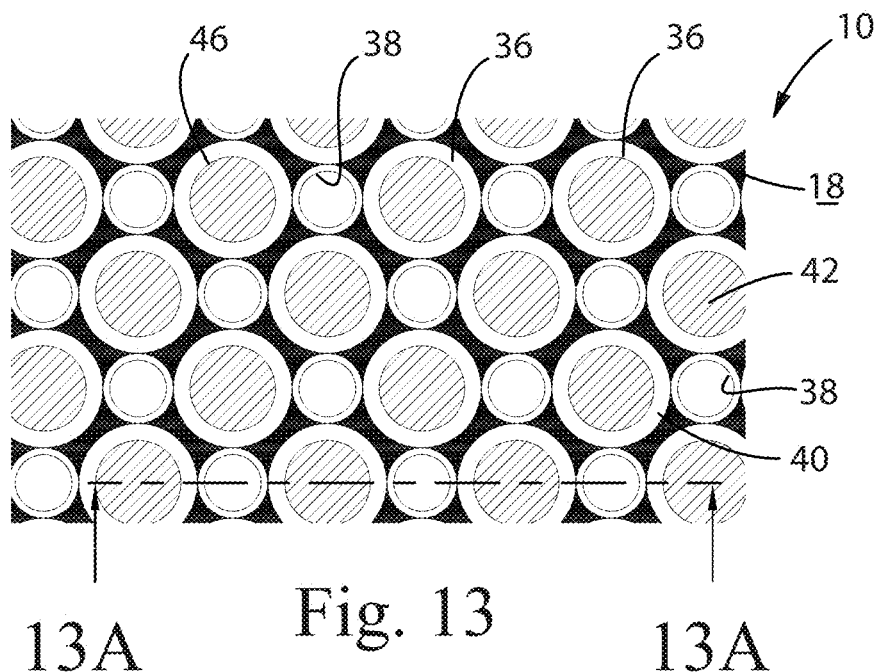
FIG. 13 is a top view of an example portion of a second roll of the pair of rolls of FIG. 1.
Figure 13A:
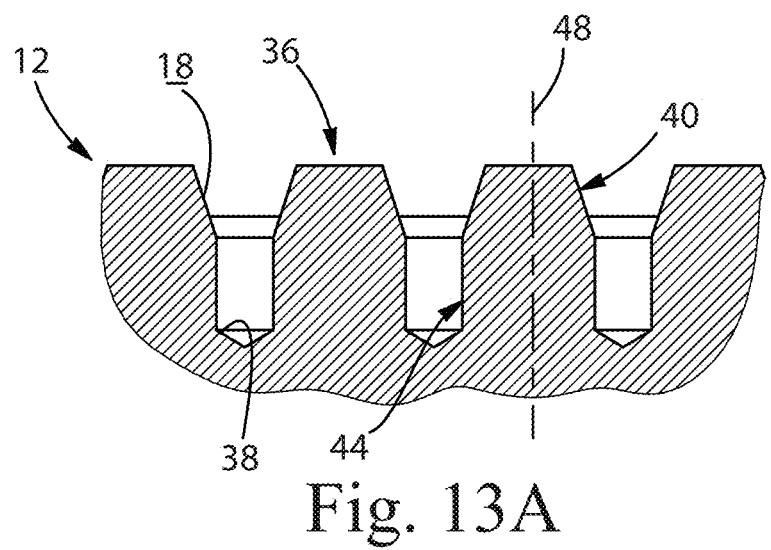
FIG. 13A is a cross-sectional view of the second roll taken about line 13A-13A of FIG. 13.
Figure 14:
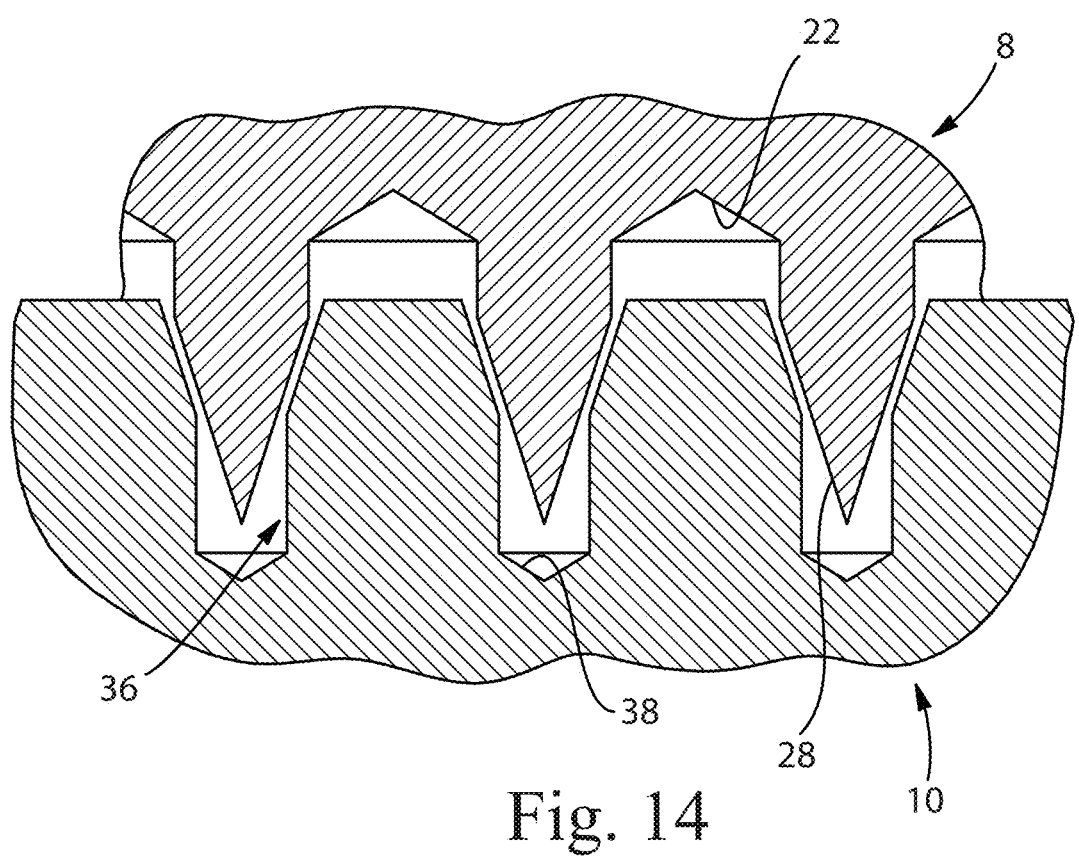
FIG. 14 is a simplified schematic cross-sectional illustration of the portion of the first roll of FIG. 12A intermeshed with the portion of the second roll of FIG. 13A.
Figure 15:
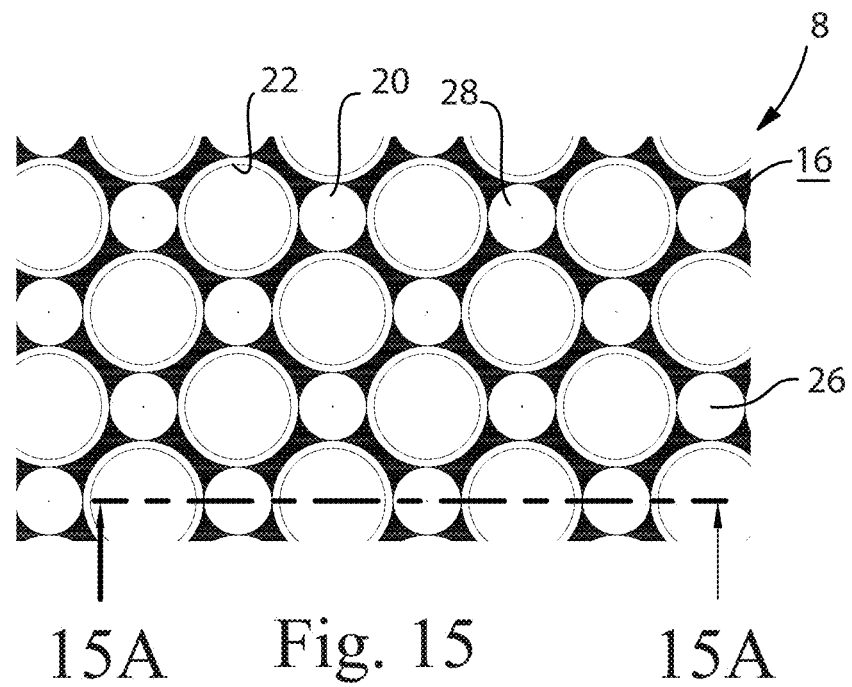
FIG. 15 is a top view of an example portion of a first roll of the pair of rolls of FIG. 1.
Figure 15A:
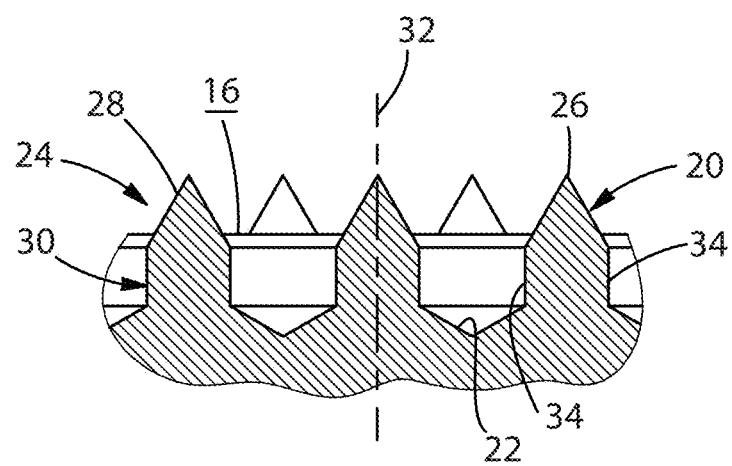
FIG. 15A is a cross-sectional view of the first roll taken about line 15A-15A of FIG. 15.
Figure 16:
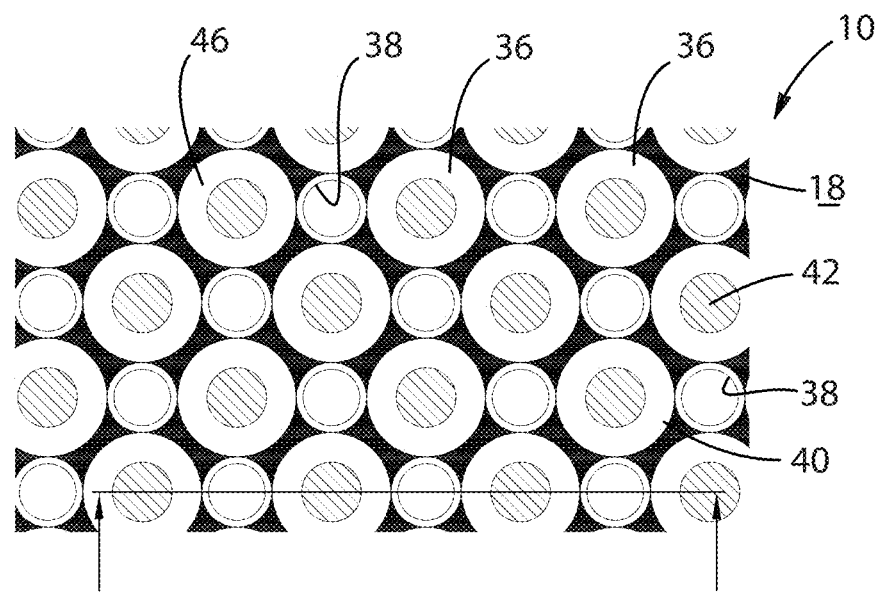
FIG. 16 is a top view of an example portion of a second roll of the pair of rolls of FIG. 1.
Figure 16A:
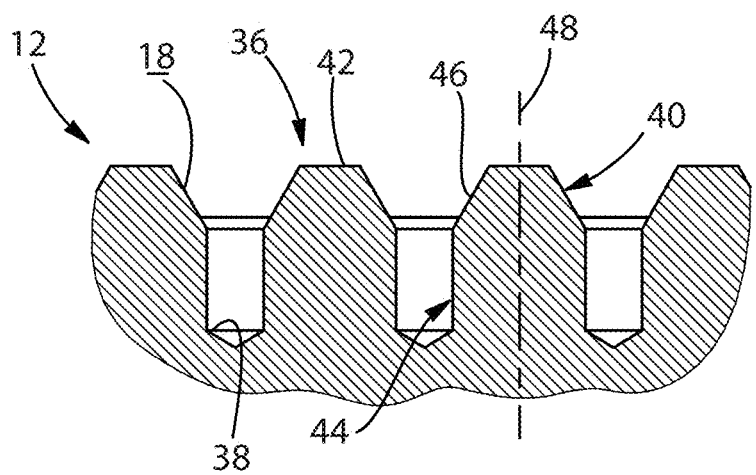
FIG. 16A is a cross-sectional view of the second roll taken about line 16A-16A of FIG. 16.
Figure 17:
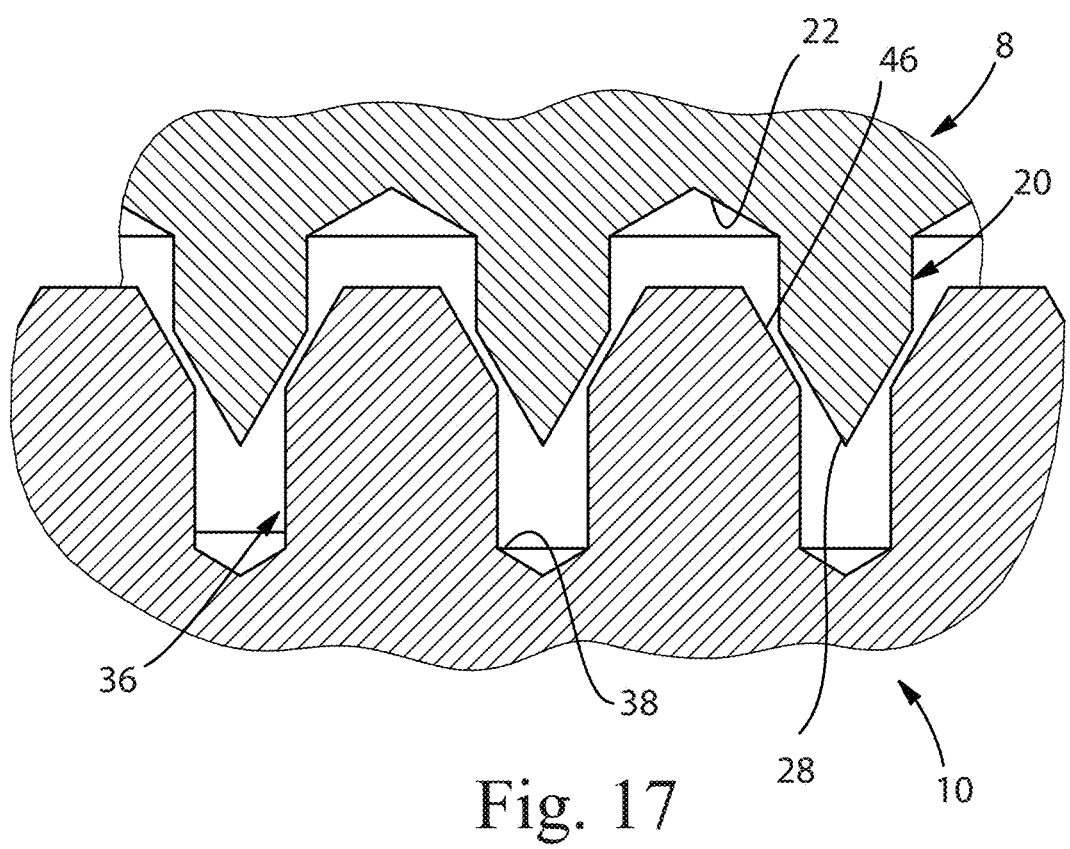
FIG. 17 is a simplified schematic cross-sectional illustration of the portion of the first roll of FIG. 15A intermeshed with the portion of the second roll of FIG. 16A.

FIGS. 9-17 illustrate other configurations of portions of the first and second rolls 8, 10 that are within the scope of the present disclosure as follows. FIG. 9 is a top view of an example portion of a first roll of the pair of rolls of FIG. 1. FIG. 9A is a cross-sectional view of the first roll taken about line 9A-9A of FIG. 9. FIG. 10 is a top view of an example portion of a second roll of the pair of rolls of FIG. 1. FIG. 10A is a cross-sectional view of the second roll taken about line 10A-10A of FIG. 10. FIG. 11 is a schematic cross-sectional example illustration of the portion of the first roll of FIG. 9A intermeshed with the portion of the second roll of FIG. 10A. FIG. 12 is a top view of an example portion of a first roll of the pair of rolls of FIG. 1. FIG. 12A is a cross-sectional view of the first roll taken about line 12A-12A of FIG. 12. FIG. 13 is a top view of an example portion of a second roll of the pair of rolls of FIG. 1. FIG. 13A is a cross-sectional view of the second roll taken about line 13A-13A of FIG. 13. FIG. 14 is a schematic cross-sectional example illustration of the portion of the first roll of FIG. 12A intermeshed with the portion of the second roll of FIG. 13A. FIG. 15 is a top view of an example portion of a first roll of the pair of rolls of FIG. 1. FIG. 15A is a cross-sectional view of the first roll taken about line 15A-15A of FIG. 15. FIG. 16 is a top view of an example portion of a second roll of the pair of rolls of FIG. 1. FIG. 16A is a cross-sectional view of the second roll taken about line 16A-16A of FIG. 16. FIG. 17 is a schematic cross-sectional example illustration of the portion of the first roll of FIG. 15A intermeshed with the portion of the second roll of FIG. 16A. In FIGS. 9-17, the same reference numbers reflect the same components as discussed with respect to FIGS. 2-4.

In some instances, the first plurality of projections, from a top view, may have a machine directional length that is shorter than a cross-directional width due to the speed at which the substrate is produced to prevent, or at least inhibit distortion in the formed apertures. Stated another way, the machine directional length may be shorter than the cross-directional width such that round apertures are formed. If the machine directional length of the first plurality of projections is the same as the cross-directional width, ovate (elongated in MD) apertures may be formed owing to the speed at which the substrate is produced. The second plurality of projections may be designed in a similar fashion for the same reason.

Figure 18:
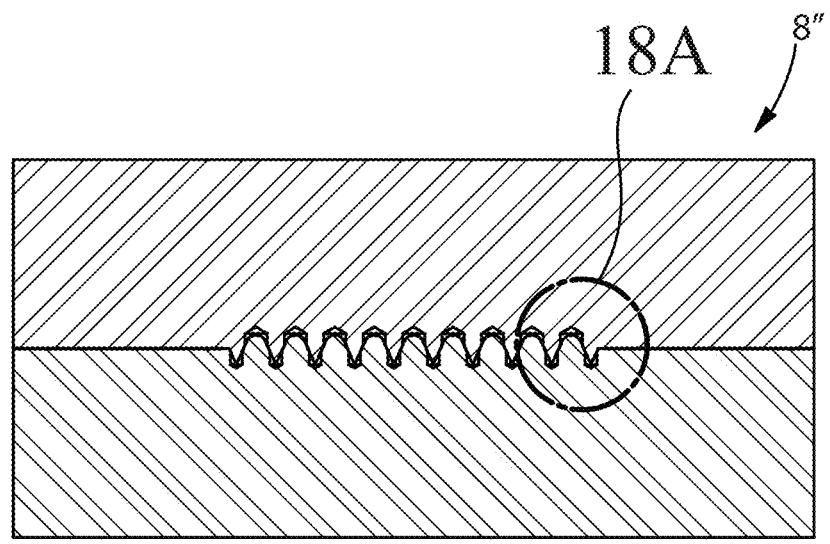
FIG. 18 is a cross-sectional view of a portion of a first roll and a portion of a second roll intermeshed with each other.
Figure 18A:
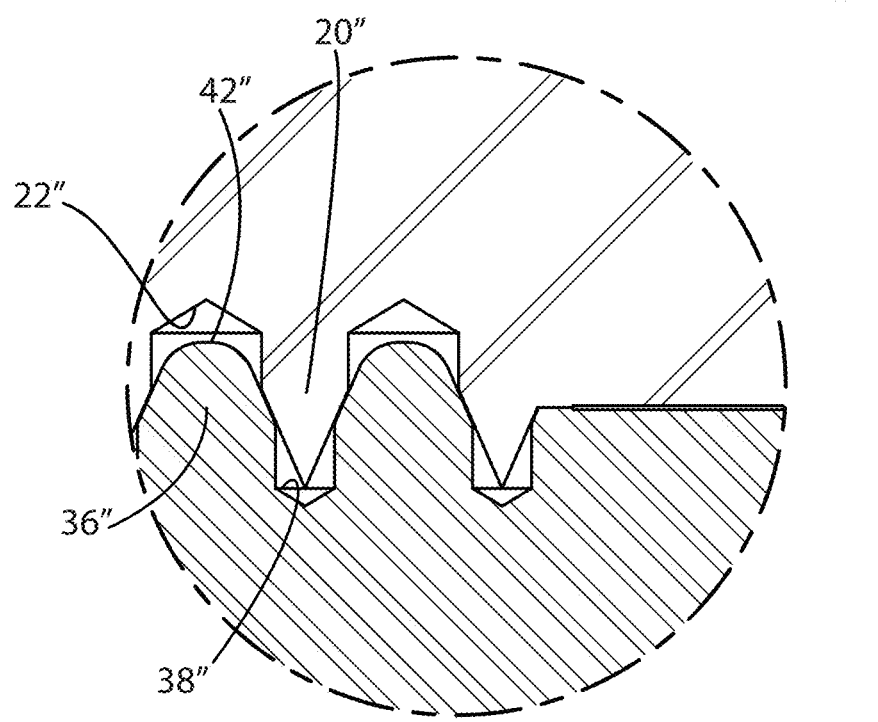
FIG. 18A is a cross-sectional blown up view of detail 18A of FIG. 18.

FIG. 18 is a cross-sectional view of a portion of a first roll 8 and a portion of a second roll 10 intermeshed with each other. FIG. 18A is a cross-sectional blown up view of detail 18A of FIG. 18. FIGS. 18 and 18A illustrate other forms of the portions of the first and second rolls 8, 10. In FIGS. 18 and 18A, the same reference numbers reflect the same components as discussed with respect to FIGS. 2-4. The second distal ends 42" of the second plurality of projections 36" have an arcuate or dome-like shape instead of a flat distal end 42 as illustrated in other figures. It is important to note that the first and second rolls of FIG. 18 illustrate a form of the rolls 8, 10 where the three-dimensional feature creation/aperturing occurs only in a middle portion of the rolls to form a central longitudinal strip of three-dimensional elements and apertures in the substrate and to form side portions without three-dimensional elements and apertures, as will be discussed in further detail below. Selective three-dimensional feature creation/aperturing may also occur in the machine direction (whether in central longitudinal strip form or not). Stated another way, in the machine direction, three-dimensional elements/apertures may be created in a first area, a second area may be free of three-dimensional elements/apertures, and then a third area may have three-dimensional elements/apertures. In the machine direction, the first area may be the most upstream and the third area may be the least upstream, with the second area being between the first and second areas. In a topsheet example, three-dimensional elements/apertures may only be created in a back waist region of the topsheet when placed in an absorbent article, for example.

The precursor substrate 4 and thereby the substrate 2 may be formed of one or more layers, for example, one or more nonwoven materials, one or more nonwoven materials and one or more film, or one or more films. If more than one layer is provided, the layers may be joined together or attached to each other through mechanical bonding, adhesive bonding, pressure bonding, heat bonding, passing heated air through both layers, or by other methods of joining to form the multilayer substrate 400. Alternatively, the layers may be formed in subsequent fiber laydown steps, such as a first and a second carding operation for a first type and a second type of staple fibers or two subsequent beams of spunlaying polymeric filaments comprising additives. The one or more layers may be the same or different in basis weight, hydrophilicity, material, fibers, density, and/or other properties. If more than one layer is present in a precursor substrate, the layers may have the same size and shape as the first layer or may have a different size and shape as the first layer. Stated another way, an additional layer may fully overlap the first layer or may only partially overlap the first layer. The layers of the precursor substrate 4 and the substrate 2 may have different colors, such as colors with different delta E values and/or different L*a*b* values. Some examples may be a white first layer and a blue second layer, a light blue first layer and a dark blue second layer, or purple first layer and a blue second layer, or first and third white layers sandwiching a blue middle layer. FIG. 19 is a top view of an example precursor substrate that may be conveyed through a nip formed between the first and second rolls 8, 10 of the present disclosure. FIG. 20 is a cross-sectional view of the precursor substrate of FIG. 19 taken about line 20-20. FIG. 21 is a cross-sectional view of the precursor substrate of FIG. 19 taken about line 21-21. FIG. 19 illustrates a precursor substrate 4 with a first layer 3 and a second layer 5. The first layer 3 is wider than the second layer 5. The second layer 5 may be positioned over or under the first layer 3 when the precursor substrate 4 is conveyed through the nip formed by the first and second rolls 8, 10. Additional layers of varying width may also be provided, such as a third layer, for example. In some instances, the second layer 5, or other layers, may be discontinuous instead of continuous as shown, such as through the use of a cut and slip process. In such an instance, the first layer 3 may be a topsheet and the second layer 5 may be an acquisition/distribution layer, for example. This may be desirable when the second layer 5 does not need to be or is not desired to be a full pitch of an absorbent article. As shown from the cross-sectional views of FIGS. 20 and 21, the second layer 5 is not as wide as the first layer 3 in the cross-machine direction. Side edges of the first layer 3 and/or the second layer 5 may not be linear and may have arcuate portions, for example. The first layer 3 may have a basis weight of in the range of about 10 gsm to about 25 gsm, about 12 gsm to about 20 gsm, about 12 gsm to about 18 gsm, about 13 gsm, about 14 gsm, about 15 gsm, about 16 gsm, about 17 gsm, specifically reciting all 0.1 gsm increments within the specified ranges and all ranges formed therein or thereby. The second layer 5 may have a basis weight in the range of about 10 gsm to about 40 gsm, about 15 gsm to about 30 gsm, about 15 gsm to about 25 gsm, about 18 gsm to about 22 gsm, about 19 gsm, about 20 gsm, about 21 gsm, specifically reciting all 0.1 gsm increments within the specified ranges and all ranges formed therein or thereby. As an example, the first layer 3 may be 175 mm wide and the second layer 5 may be 95 mm wide. In an instance, the first layer 3 may comprise two side pieces that are attached to side portions of the second layer 5, such that a three piece substrate is formed.

An example precursor substrate may have a first layer and a second layer (or any other suitable number of layers, such as one layer or three layers). The first layer may comprise a plurality of first fibers and/or filaments (sometimes referred to herein together as "fibers"). The plurality of first fibers may comprise fibers that are the same, substantially the same, or different in size, shape, composition, denier, fiber diameter, fiber length, and/or weight. The second layer may comprise a plurality of second fibers. The plurality of second fibers may comprise fibers that are the same, substantially the same, or different in size, shape, composition, denier, fiber diameter, fiber length, and/or weight. The plurality of first fibers may be the same as, substantially the same as, or different than the plurality of second fibers. Additional layers may have the same or different configurations.

The first layer and/or the second layer may comprise bicomponent fibers having a sheath and a core. The sheath may comprise polyethylene and the core may comprise polyethylene terephthalate (PET). The sheath and the core may also comprise any other suitable materials known to those of skill in the art. The sheath and the core may each comprise about 50% of the fibers by weight of the fibers, although other variations (e.g., sheath 60%, core 40%; sheath 30%, core 70% etc.) are also within the scope of the present disclosure. The bicomponent fibers or other fibers that make up the first and/or second layers may have a denier in the range of about 0.5 to about 10, about 0.5 to about 6, about 0.75 to about 4, about 1.0 to about 4, about 1.5 to about 4, about 1.5 to about 3, about 1.5 to about 2.5, or about 2, specifically including all 0.1 denier increments within the specified ranges and all ranges formed therein or thereby.

Denier is defined as the mass in grams per 9000 meters of a fiber length. In other instances, the denier of the fibers of the first layer may be in the range of about 1.5 denier to about 6 denier or about 2 denier to about 4 denier and the denier of the fibers of the second layer may be in the range of about 1.2 denier to about 3 denier or about 1.5 denier to about 3 denier, specifically reciting all 0.1 denier increments within the specified ranges and all ranges formed therein or thereby. In certain instances, the fibers of the first layer may be at least 0.5 denier, at least 1 denier, at least 1.5 denier, or at least 2 denier greater than the denier of the fibers of the second layer depending at least in part on the particular acquisition and/or distribution system in use in a certain absorbent article. By providing the fibers of the first layer with a denier higher than a denier of the fibers of the second layer, a pore gradient is provided in the liquid permeable substrate. This pore gradient may provide better dryness and/or acquisition in the liquid permeable substrate. The fibers having the larger denier in the first layer provide larger pores than the fibers having the smaller denier in the second layer, thereby producing the pore gradient between the layers.

The plurality of first and second fibers may also comprise any other suitable types of fibers, such as polypropylene fibers, other polyolefins, other polyesters besides PET such as polylactic acid, thermoplastic starch-containing sustainable resins, other sustainable resins, bio-PE, bio-PP, and Bio-PET, viscose fibers, rayon fibers, or other suitable nonwoven fibers, for example. These fibers may have any suitable deniers or denier ranges and/or fiber lengths or fiber length ranges. In an instance where the plurality of first and second fibers are the same or substantially the same, the plurality of second fibers may be treated with a hydrophilic agent, such as a surfactant, to cause the plurality of second fibers to become hydrophilic or at least less hydrophobic. The plurality of first fibers may not be treated with the surfactant such that they remain in their natural hydrophobic state or the plurality of first fibers may be treated with a surfactant to become less hydrophobic.

The first layer may have a basis weight in the range of about 10 gsm to about 25 gsm. The second layer may have a basis weight in the range of about 10 gsm to about 45 gsm. The basis weight of the substrate (both first and second layers) may be in the range of about 20 gsm to about 70 gsm, about 20 gsm to about 60 gsm, about 25 gsm to about 50 gsm, about 30 gsm to about 40 gsm, about 30 gsm, about 35 gsm, or about 40 gsm, for example.

In a form, the basis weight of the precursor substrate 4 may be about 30 gsm to about 40 gsm or about 35 gsm. In such an example, the first layer may have a basis weight in the range of about 10 gsm to about 20 gsm, or about 15 gsm, and the second layer may have a basis weight in the range of about 15 gsm to about 25 gsm, or about 20 gsm. In another example, the basis weight of the substrate may be about 20 gsm. In such an example, the first layer may have a basis weight of about 10 gsm and the second layer may have a basis weight of about 10 gsm. In still another example, the basis weight of the substrate may be about 60 gsm. In such an example, the first layer may have a basis weight of about 24 gsm, and the second layer may have a basis weight of 36 gsm. All other suitable basis weight ranges for the first and second layers and the substrates are within the scope of the present disclosure. Accordingly, the basis weight of the layers and the substrates may be designed for specific product requirements.

Specifically recited herein are all 0.1 gsm increments within the above-specified ranges of basis weight and all ranges formed therein or thereby.

In some instances, it may be desirable to have a higher basis weight in the first layer compared to the second layer. For instance, the first layer's basis weight may be at least about 1 to about 4 times, at least about 1 to about 3.5 times, about 1.5 to about 3 times, about 1.5 times to about 3 times, about 2 times, about 2.5 times, or about 3 times greater than the second layer's basis weight. In some instances, the basis weight of the first layer may be in the range of about 20 gsm to about 30 gsm, and the basis weight of the second layer may be in the range of about 10 gsm to about 20 gsm, for example. Specifically recited herein are all 0.1 gsm increments within the above-specified ranges of basis weight and all ranges formed therein or thereby. By providing the first layer (hydrophobic) with a higher basis weight than the second layer (hydrophilic), more hydrophobic material than hydrophilic material is provided in the liquid permeable substrate. Upon information and belief, more hydrophobic material and less hydrophilic material in the liquid permeable substrate provides for better acquisition and/or dryness. The surface tension of the hydrophilic layer may be reduced to at least inhibit the hydrophilic layer (second layer) from contaminating the hydrophobic layer (first layer) (and making it more hydrophilic) upon the liquid permeable substrate receiving one or more gushes.

The fibers may be spunbond fibers, hydroentangled fibers, carded fibers, meltblown fibers, nano fibers (less than 1 micron), or other suitable types of fibers. The fibers may be crimped. The fibers may have a circular cross-sections or non-circular shaped cross section, such as ovate or trilobal, for example.

In an example, referring to FIG. 19, the first layer 3 and the second layer 5 may together form a topsheet of an absorbent article. The first layer 3 may be on the baby-facing surface or the wearer-facing side. The first layer 3 (wearer-facing side) may be hydrophobic and the second layer 5 may be hydrophilic (garment-facing side) or the second layer 5 may be hydrophobic (wearer-facing side) and the first layer 3 may be hydrophilic (garment-facing side). In some configurations, both of the layers 3, 5 (or other layers) may be hydrophobic or hydrophilic to the same degree or to different degrees. Either or both of the layers 3, 5 may have the three-dimensional elements and/or apertures described herein. In an instance where both of the layers 3, 5 have the three-dimensional elements and the apertures, the three-dimensional elements and apertures may be formed in/through both layers. When the precursor substrate 4 is conveyed through the nip, the two layers 3, 5 (or other layers) may be joined together by the first and second rolls 8, 10 without the use of an adhesive. In other instances, adhesives may be used to join the various layers.

In some instances, bonds 9 may be formed around portions of the perimeter of the second layer 5 to help join the second layer 5 to the first layer 3. The bonds 9 may also be formed in other areas where the first and second layers overlap. The bonds 9 may be compressed areas in the first and second layers 3, 5. The bonds 9 may be applied to the first and second layers (or to additional layers) upstream of the nip, in the nip (i.e., by the first and second rolls 8, 10), or downstream of the nip. Tooling for applying the bonds 9 may be a pair of rolls having nubs on one roll and a flat surface or nubs on the other roll. If nubs are provided on both rolls, they may come into contact with each other to form the bonds 9. The first and second rolls 8, 10 may comprise the nubs and/or flat surfaces if the bonds 9 are going to be applied in the nip.

In some instances, the substrates produced by the methods and tooling of the present disclosure may be used as outer cover materials for absorbent articles or as other portions of absorbent articles.

The precursor web 4 and/or the substrate 2 (after the nip between the first and second rolls 8, 10) may be subjected to a variety of treatments. Some example treatments are chemical treatments, mechanical treatments, and/or heat treatments. Examples of chemical treatments may be applying one or more lotions, surfactants, vitamins, pH modifiers, inks, enzymes, hydrophilic materials, hydrophobic materials, and/or other substances either before, after, or in the nip between the first and second rolls 8, 10. These chemical treatments may be sprayed onto the precursor substrate or substrate, rolled onto the precursor substrate or substrate, applied by one or more of the first and second rolls 8, 10 or portions thereof, and/or may be applied by other methods. In some instances, the chemical treatments may be applied to the first and/or second plurality of projections 20, 36 and then transferred to the substrate in the nip. As an example, a hydrophobic composition may be applied to the precursor substrate 4 upstream of the nip and then the first distal portions 24 of at least some of the first plurality of projections 20 may be coated with a hydrophilic treatment that may be transferred to perimeters of apertures formed by the projections 20. In such an instance, the substrate 2 may be primarily hydrophobic but have hydrophilic areas on or proximate to perimeters of the apertures. Examples of mechanical treatments may be embossing, cross-machine direction tensioning, and/or machine direction tensioning either before or after the nip. Such mechanical treatments may be applied by other rolls or other equipment upstream and/or downstream from the first and second rolls 8, 10. Examples of heat treatments may comprise heating the precursor substrate 4 before the nip, heating the precursor substrate in the nip, and/or heating the substrate after the nip. The precursor substrate 4 or the substrate 2 may be heated by blowing hot air through the precursor substrate 4 or substrate 2 (i.e., "air-through), by running the entire precursor substrate 4 or substrate 2 through a heat tunnel, by running a surface of the precursor substrate 4 or substrate 2 over a heated roll (to only heat the surface) or a nip between two heated rolls (to heat both surfaces), by radiation, and/or by heating the first and/or second rolls 8, 10, for example. Hot air may also be blown through conduits in one or more of the rolls 8, 10, to heat the precursor substrate 4. Heating the precursor substrate 4 before the precursor substrate 4 enters the nip may cause the precursor substrate 4 to absorb enough heat to allow the precursor substrate 4 or polymers in the precursor substrate 4 to flow under pressure and create bonds to stabilize the apertures 56 and/or three-dimensional elements 54. Heating the substrate 2 after the nip may cause the three-dimensional elements 54 and the apertures 56 to be "set" into the substrate. In some cases, it may be desirable to input energy into the precursor substrate or substrate to either aid in the formation of the three-dimensional elements 54 and apertures 56 and/or to help "set" the three-dimensional elements and/or apertures. This input energy may also help to stabilize the substrate and may promote better fiber fusion in the substrate. Providing input energy to the substrate may also provide the three-dimensional elements of the substrate, or the substrate as a whole, the ability to better resist compression due to packaging.

If the precursor substrate 4 is heated upstream of the nip, it may be cooled in the nip or downstream from the nip.

Cooling may be accomplished by maintaining the first and second rolls 8, 10 at ambient temperature, by running the substrate 2 over a cooled roll, or by cooling the first and second rolls 8, 10. The first and second rolls 8, 10 may be at a temperature cooler than a temperature of the precursor substrate. Cooling may also be accomplished in the nip by blowing ambient or cooled air into the nip. Cooling may also be accomplished by ambient air or by blowing ambient air onto the substrate downstream of the nip or by providing a cooling source, such as cooled air blowing on the substrate or by cooled rolls. Cooling may also be accomplished through cooling in the nip (cooled first and second rolls 8, 10) and downstream of the nip (cooled rolls, blowing ambient air, or blowing cooled air).

If the precursor substrate 4 is heated in the nip, it may be cooled downstream of the nip. Cooling may be accomplished downstream of the nip by ambient air, by blowing ambient air, or by providing a source of cooling, such as blown cooled air or cooled rolls.

Figure 22:
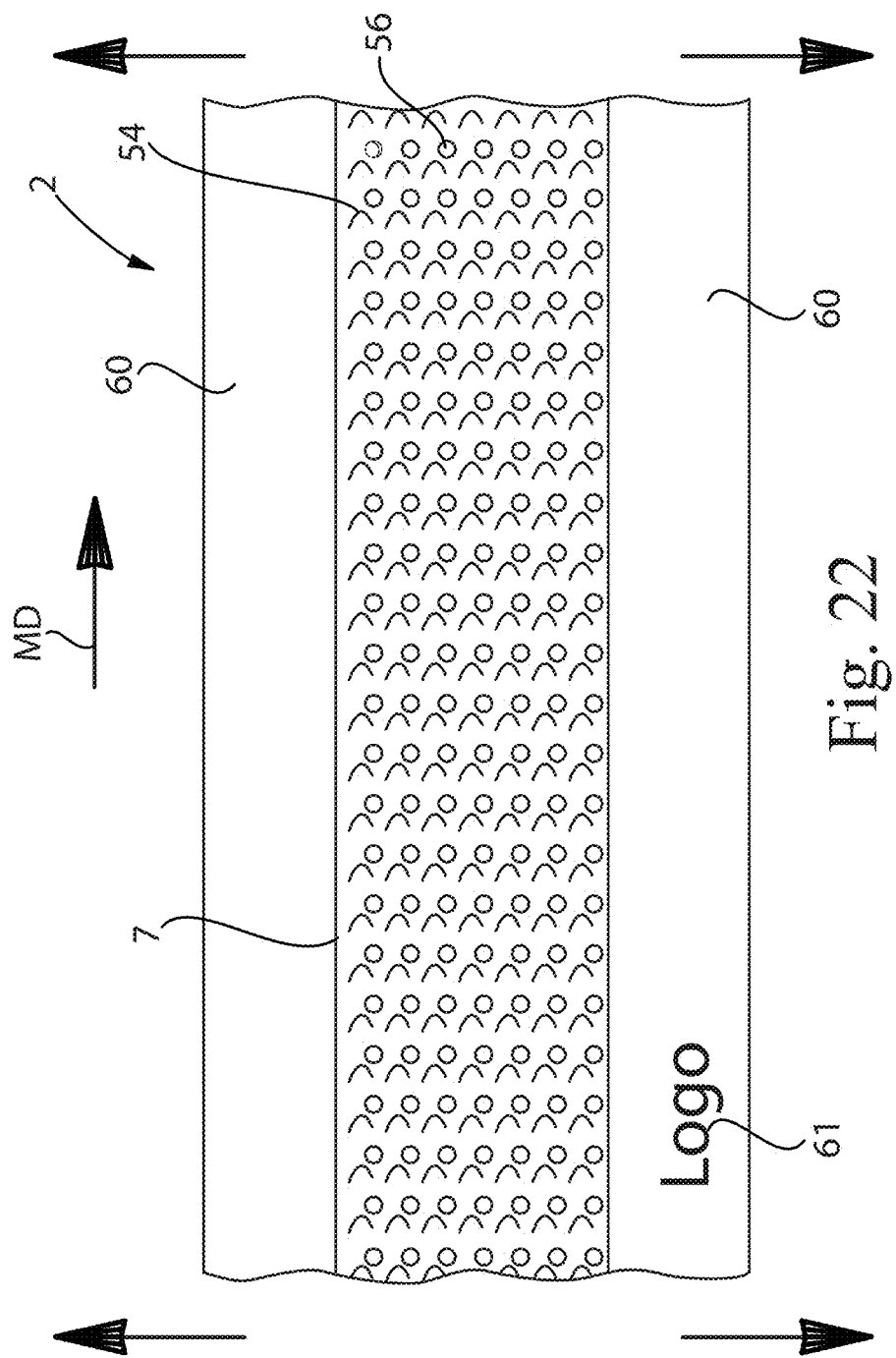
FIG. 22 is a top view of an example substrate after being conveyed through the nip and having a central longitudinal strip comprising three-dimensional elements and apertures.

Referring now to FIG. 22, a top view of a continuous substrate 2 is illustrated. This substrate 2 is after the three-dimensional elements 54 and/or the apertures 56 were formed in the substrate 2 by the first and second rolls 8, 10. The three-dimensional elements 54 and apertures 56 are shown generically in FIG. 22 for purposes of illustration only. The substrate 2 may be formed of one or more layers, as referenced herein. The two layers may have the same cross-machine directional width or a different cross-machine directional width. The cross-machine direction in FIG. 22 is perpendicular to arrow "MD". In an instance, an additional layer or a second layer may be placed only in a central longitudinal strip 7 in the substrate 2.

Figure 23:
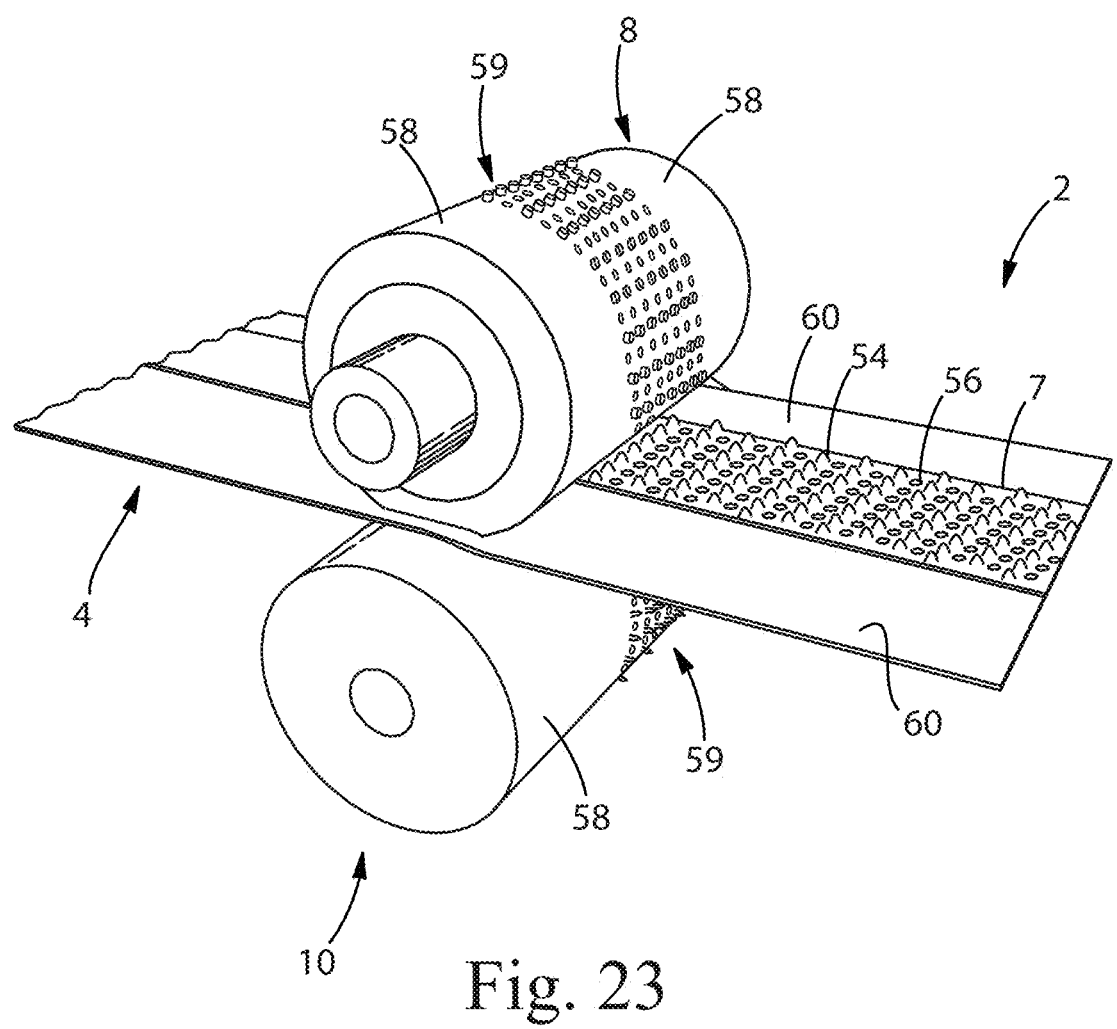
FIG. 23 illustrates first and second rolls that may create a substrate having a central longitudinal strip as illustrated in FIG. 22.

In a single layer format, or a two or more layer format, where all of the layers have the same cross-machine directional width, the three-dimensional elements 54 and/or the apertures 56 may be formed only in the central longitudinal strip 7 with the areas outside the central longitudinal strip 7 being free of the three-dimensional elements 54 and/or the apertures 56. As such, a method may comprise only contacting the central longitudinal strip 7 of the precursor substrate 4 with portions of the first plurality of projections 20, portions of the first plurality of recesses 22, portions of the second plurality of projections 36, and portions of the second plurality of recesses 38. As such, the first and second rolls 8, 10 may have the example configuration illustrated in FIG. 23 with first areas 58 away from a center of the rolls 8, 10 being free of any projections or any recesses and with second areas 59 proximate to the center of the rolls 8, 10 comprising the first and second plurality of projections 20, 36 and the first and second pluralities of recesses 22, 38. As a result, the three-dimensional elements 54 and/or the apertures 56 may only be formed in the central longitudinal strip 7 of the substrate 4. In one instance, a logo, brand name, or other indicia 61 may be formed in the side portions 60 and/or in the central longitudinal strip 7. This logo, brand name, or other indicia 61, may be formed using the tooling described herein or by embossing, for example. In any event, the logo, brand name, or other indicia 61 may have three-dimensional elements or may be formed of three-dimensional elements, recesses, and/or apertures.

In a two or more layer precursor substrate, where one layer has a different cross-machine directional width as the other layer or layers, the three-dimensional elements 54 and/or the apertures 56 may be formed only where there is overlap between the layers, such as in a central longitudinal strip 7 or in another portion. In such an instance, a method may comprise conveying a first precursor web in a machine direction, conveying a second precursor web in the machine direction either under or over the first precursor web. The first and second precursor webs may be joined by bonds, through-air bonds, adhesives, or may merely be on contact with each other and joined together in the nip. The first precursor web may have a first cross-machine directional width and the second precursor web may have a second, smaller cross-machine directional width. The method may comprise contacting the precursor substrate and the second precursor substrate with portions of the first plurality of projections, portions of the first plurality of recesses, portions of the second plurality of projections, and portions of the second plurality of recesses in the nip substantially only, or only, where the first precursor substrate overlaps with the second precursor substrate. The resulting substrate would also have the appearance show in FIG. 22 with two layers of material in the central longitudinal strip 7 and one layer outside the central longitudinal strip 7.

Once the three-dimensional elements 54 and/or the apertures 56 are formed in the central longitudinal strip 7 (whether one or more layers), side portions 60, or areas thereof, free of the three-dimensional elements 54 and/or the apertures 56 may be stretched in the cross-machine direction to reduce the basis weight of the side portions 60. If the substrate is used as a topsheet in an absorbent article, such as a diaper or adult incontinence article, at least areas of the side portions 60 may be positioned under leg cuffs of the absorbent article. As such, these areas of the side portions 60, or the entire side portions 60, may not contact a wearer's skin and may not be visible to a consumer or caregiver. As a result, material savings may be achieved by stretching at least the areas, or the entire side portions, in the cross-machine direction. As an example, if the side portions 60 prior to stretching have a basis weight of 15 gsm (grams per square meter), the side portions 60 may be stretched in the cross-machine direction such that their basis weight becomes 10 gsm. This cross-machine directional stretching may be accomplished in a number of ways.

Figure 24:
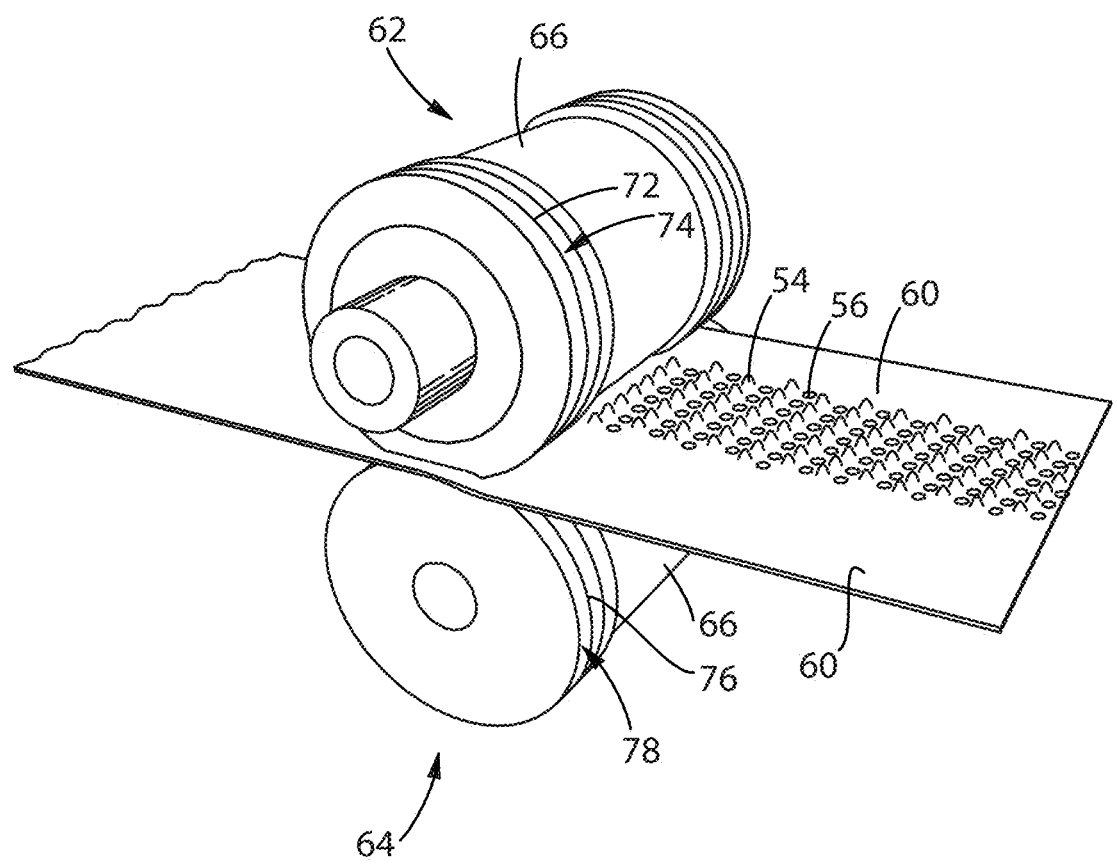
FIG. 24 is a perspective view of two stretching rolls for stretching side portions of the substrate of FIG. 22.
Figure 25:
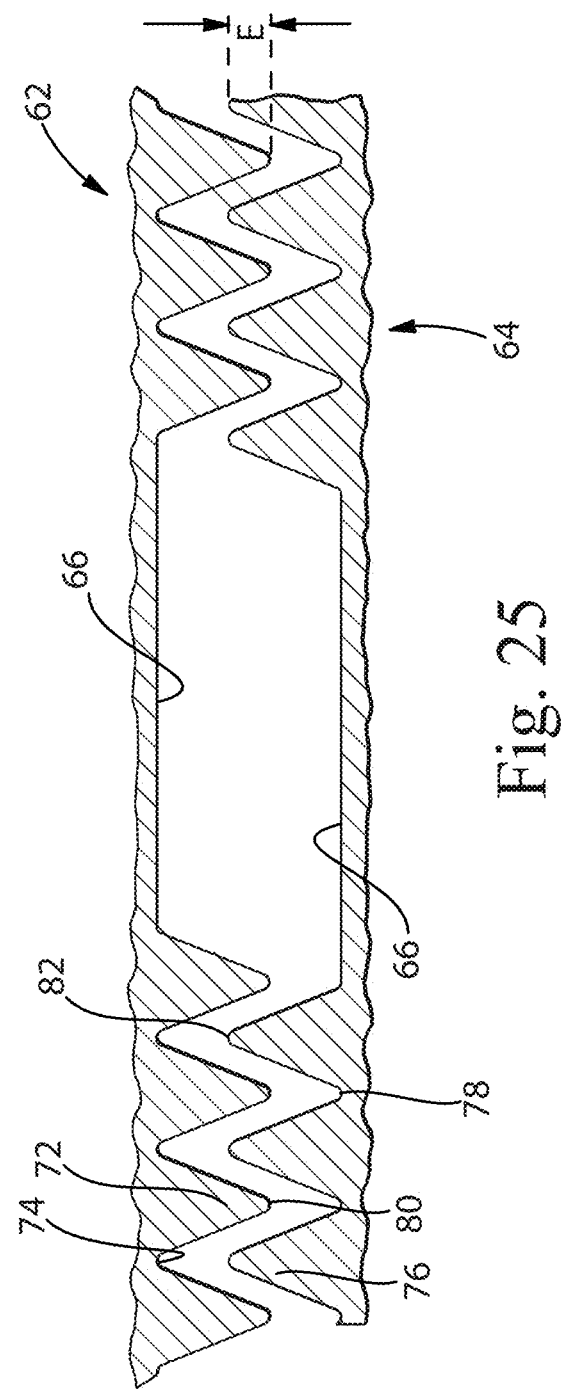
FIG. 25 is a cross-sectional illustration of ridges and grooves in each of the rolls of FIG. 24.

Referring to FIGS. 24 and 25, one suitable example way of cross-machine directional stretching the side portions 60, or portions thereof, may be accomplished using a first stretching roll 62 and a second stretching roll 64. The first and second stretching rolls 62 and 64 may each have middle portions 66 that are generally radial without having any three-dimensional elements. The first stretching roll 62 may comprise a first plurality of ridges 72 and a first plurality of grooves 74 in the outer portions 68, 70. The second stretching roll 64 may comprise a second plurality of ridges 76 and a second plurality of grooves 78 in the outer portions 68, 70. At least some of, or all of, the first plurality of ridges 62 on the first roll 62 may engage at least some of, or all of, the second plurality of grooves 78 on the second roll 64. Likewise, at least some of, or all of, the second plurality of ridges 76 on the second roll 64 may engage at least some of, or all of, the first plurality of grooves 74 on the first roll 62. The tips 80 of the first plurality of ridges 72 on the first roll 62 may enter the second plurality of grooves 78 on the second roll 64 to a certain depth of engagement "E". Likewise, the tips 82 of the second plurality of ridges 76 on the second roll 64 may enter the first plurality of grooves 74 on the first roll 62 to the certain depth of engagement, E. The depth of engagement, E, controls the degree to which the side portions 60 are stretched in the cross-machine direction. A lower depth of engagement results in less cross-machine directional stretching and a higher depth of engagement results in more cross-machine directional stretching. As result, the degree of cross-machine directional stretching of the side portions 60 may be varied according to the depth of engagement, E.

The side portions 60 of the substrate 2 may be positioned intermediate the outer portions 68 and 70 on the first and second stretching rolls 62 and 64. The central longitudinal strip 7 may be positioned intermediate the middle portions 66 of the first and second stretching rolls 62 and 64. In such a fashion, the central longitudinal strip 7 may not be stretched in the cross-machine direction while the side portions 60 may be stretched in the cross-machine direction. Further, in this fashion, the central longitudinal strip 7 may not actually be in contact with the middle portions 66 of the rolls 62, 64 so that the three-dimensional elements 54 within the central longitudinal strip 7 are not compressed.

In a two layer configuration, with the second layer only being present in the central longitudinal strip, a method may comprise stretching the first layer in a cross-machine direction where, or only where, the first layer is free of overlap with a second layer (i.e., outside the central longitudinal strip). This stretching step may occur upstream of the nip or downstream of the nip.

Again referring to FIG. 22, the substrate 2 (whether having three-dimensional elements 54 and apertures 56 in a central longitudinal strip or throughout the substrate 2) may be cut to a final pitch for a component of an absorbent article, such as a topsheet, an acquisition layer, a distribution layer, or an outer cover nonwoven material, for example. The substrate 2 may be cut along line 88. Although line 88 is illustrated as perpendicular to the machine direction, those of skill in the art will recognize that the actual cut path may not perpendicular to the machine direction, but instead may be transverse to the machine direction to account for the speed of the moving substrate during cutting. Stated another way, the cut path may be angled with respect to the cross-machine direction to account for substrate speed on the absorbent article manufacturing line. The cut substrates may then be joined to a portion of an absorbent article on the absorbent article manufacturing line.

Referring again to FIG. 22, the central longitudinal strip 7 may be a layer placed on another layer. In an example of a topsheet, the topsheet may have a solid, generally planar layer on a garment-facing surface thereof and a patch of the central longitudinal strip 7 on a wearer-facing surface thereof. The patch may comprise a precursor substrate run through the nip between the first and second rolls 8, 10 thereof and containing the three-dimensional elements 54 and/or the apertures 56. The patch may or may not be the full absorbent article pitch. Stated another way, the patch may not be the full length of the topsheet and/or the absorbent article. Also, the patch may or may not be the full width of the topsheet.

Figure 26:
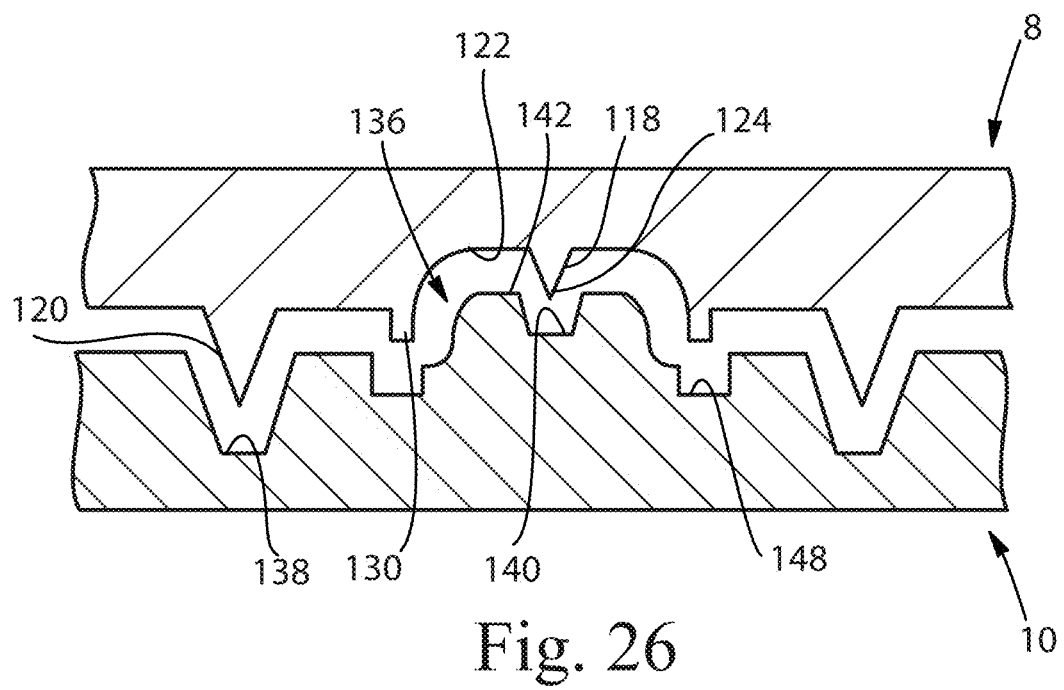
FIG. 26 is a cross-sectional illustration of alternative example rolls for creating three-dimensional elements and apertures in the precursor substrate.
Figure 27:
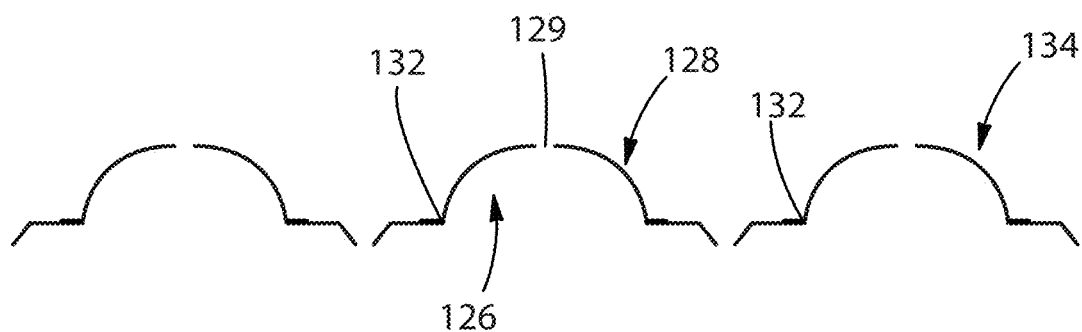
FIG. 27 is a cross-sectional illustration of a three-dimensional substrate with apertures produced by the rolls of FIG. 26.

FIG. 26 is a cross-sectional illustration of alternative portions of example first and second rolls 8, 10 for creating three-dimensional elements and apertures in the precursor substrate. FIG. 27 is a cross-sectional illustration of a three-dimensional substrate 134 with apertures produced by the first and second rolls of FIG. 26. Referring to FIG. 26, the first roll 8 may comprise a first plurality of projections 120 (which could be like or similar to the first plurality of projections 20 discussed herein, including the bases, the first distal portions, and the first distal ends) and a first plurality of recesses 122. At least some of, or all of, the recesses of the first plurality of recesses 122 may comprise an aperture forming projection 118. The aperture forming projection 118 may be conical or any other suitable shape configured to form an aperture. The aperture forming projection 118 may comprise a point 124 (as "point" is described herein) to aid in the formation of apertures in the precursor substrate 4. The aperture forming projections 118 may be configured to form apertures 129 in three-dimensional elements 128 of the precursor substrate 4. It may be desirable to have the apertures 129 in the three-dimensional elements 128 to allow fluids (e.g., urine, menses, runny BM) to access void volumes 126 that form on the underside of the three-dimensional elements 128 and at least inhibit fluids from remaining in contact with the skin of a wearer. The first roll 8 may comprise a densifying projection 130 about at least a portion of, or all of, a perimeter of at least some of the first plurality of recesses 122. Stated another way, the densifying projection 130 may fully surround the recesses 122 or may only partially surround the recesses 122. The densifying projection 130 may be continuous or discontinuous. The densifying projection 130 may be used to create compressed regions or densified areas 132 in the precursor substrate 4. By having the compressed regions or densified areas 132 in the substrate 4, the three-dimensional elements 128 may be stabilized.

Referring again to FIGS. 26 and 27, the second roll 10 may comprise a second plurality of projections 136 and a second plurality of recesses 138 (which could be like or similar to the second plurality of recesses 22 discussed herein). At least some of the second plurality of projections 136 may comprise a recess 140 defined in second distal ends 142 thereof. The recesses 140 are configured to at least partially receive at least a portion of the aperture forming projection 118, including the point 124, to aperture the three-dimensional elements 128. The second roll 10 may comprise one or more recesses 148 for receiving at least a portion of the densifying projection 130. The recesses 148 may or may not fully surround the projections 136 and may be continuous or discontinuous.

Figure 28:
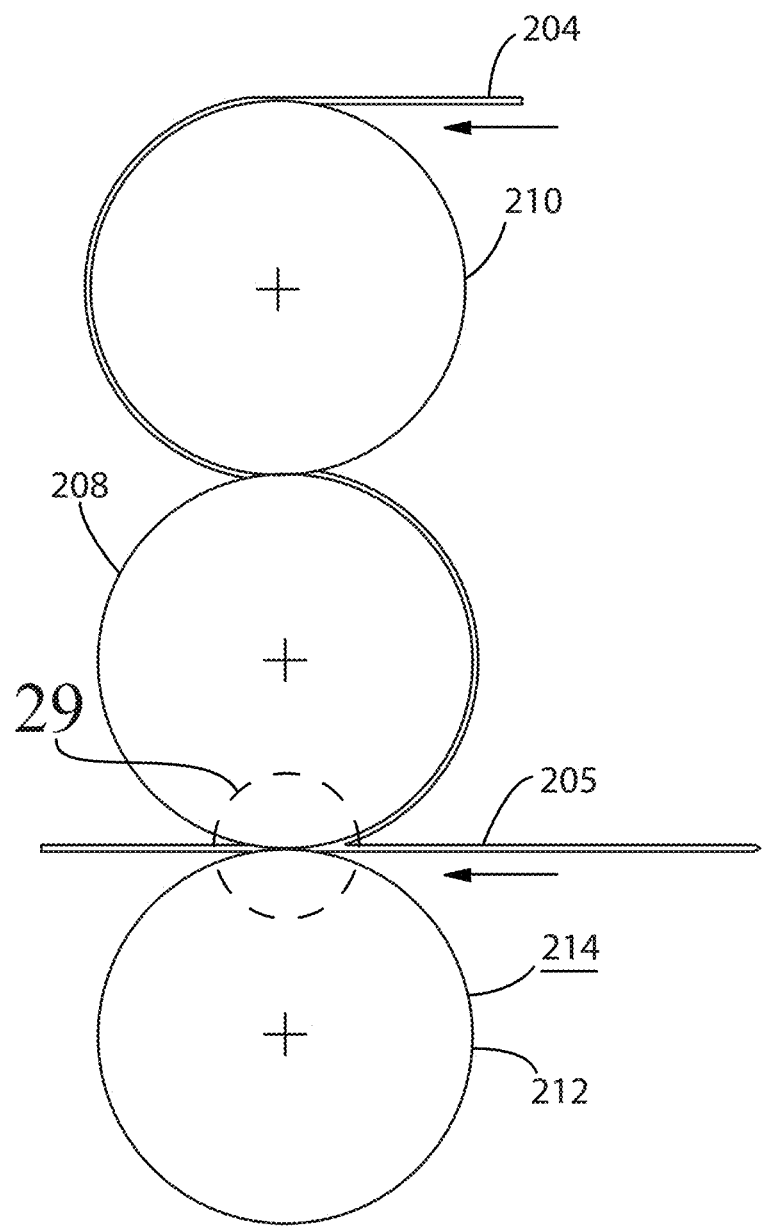
FIG. 28 is a schematic illustration of a three roll process of creating a substrate having a first substrate with three-dimensional elements and apertures and a second generally planar substrate with only apertures.
Figure 29:
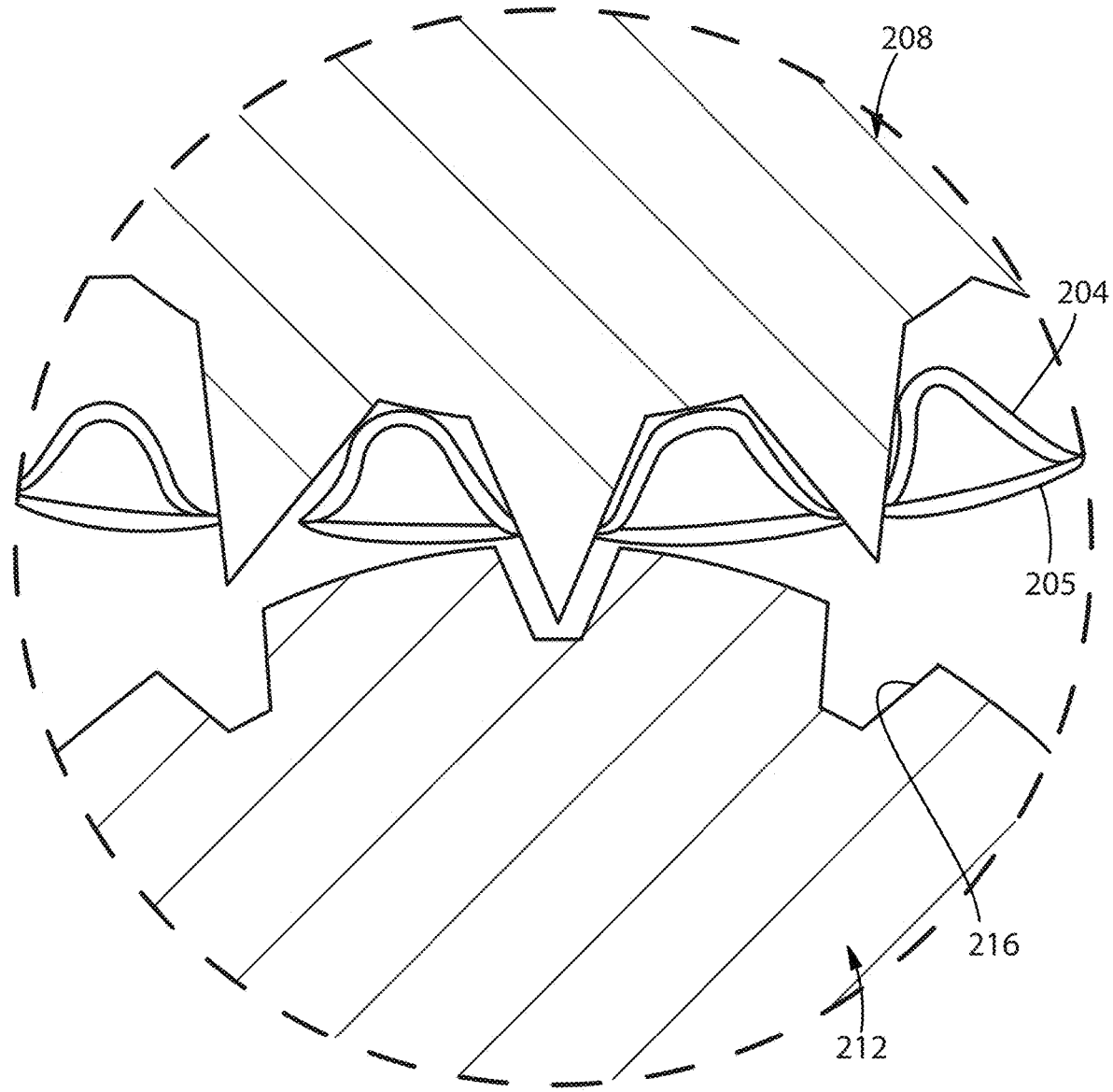
FIG. 29 is a cross-sectional view taken about detail 29 of FIG. 28.

FIG. 28 is a schematic illustration of a three roll process of creating a substrate having a first substrate with three-dimensional elements and apertures and a second generally planar substrate with only apertures. FIG. 29 is a cross-sectional view taken about detail 29 of FIG. 28. In FIG. 28, the first roll 208 and the second roll 210 may be the same as the first and second rolls 8, 10 described herein are illustrated simply in FIG. 28. The third roll 212 may be a roll having a radial outer surface 214 with a plurality of recesses 216 defined therein. The recesses in the third roll 212 may the same as or similar to the recesses of the first plurality of recesses 22 in the first roll 8. The third roll 212 may not have any projections. In such a three roll process, a precursor substrate 204 may be conveyed between the first and second rolls 208 and 210 to form the three-dimensional elements and apertures described herein. The precursor substrate 204 may then continue to rotate around the first roll 208 with the first plurality of projections 20 engaged with the precursor substrate 204. The second precursor substrate 205 is conveyed into a nip formed between the first roll 208 and the third roll 212. The projections 20 then enter the recesses 216 in the third roll to puncture apertures in the second precursor substrate 205 in the nip between the first roll 208 and the third roll 212. An example resulting structure is illustrated in the nip of FIG. 29.

The second substrate 205 may be generally planar with apertures after being conveyed through the nip between the first and third rolls 208 and 212. The resulting structure is a two substrate composite with a three-dimensional top substrate 204 and a generally planar bottom substrate 205. Apertures will extend through both of the substrates 204, 205 as a result of the first and third rolls 208 and 212. As an example the three-dimensional top substrate 204 may be a topsheet and the generally planar bottom substrate 205 may be an acquisition layer. As another example the three-dimensional top substrate 204 may be part of a topsheet and the generally planar bottom substrate 205 may be part of an acquisition layer. The three-dimensional top substrate 204 and the generally planar bottom substrate 205 may each be formed of one or more layers or materials.

The two substrate laminate provides integrity to the structure and locks in the three-dimensional elements and apertures. The first and second substrates 204, 205 may be free of thermally shrinkable fibers. One or more adhesives may be sprayed onto or otherwise applied to the second precursor substrate 205 to cause it to adhere to the first precursor substrate 204 in the nip. In some instances, adhesives may not be required between the first and second precursor substrates 204, 205. In such an instance, the forces of the nip between the first and third rolls and the aperturing process may be enough to join the two layers.

Figure 30:
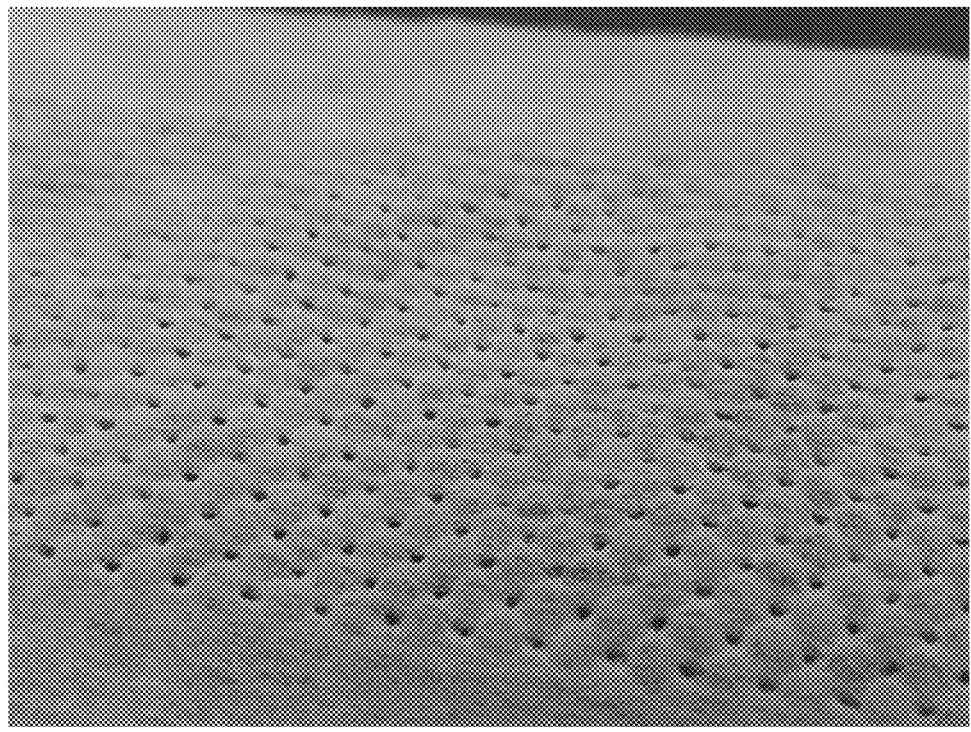
FIG. 30 is a top perspective view of an example three-dimensional apertured substrate produced by the first and second rolls 8, 10 of FIG. 1.
Figure 31:
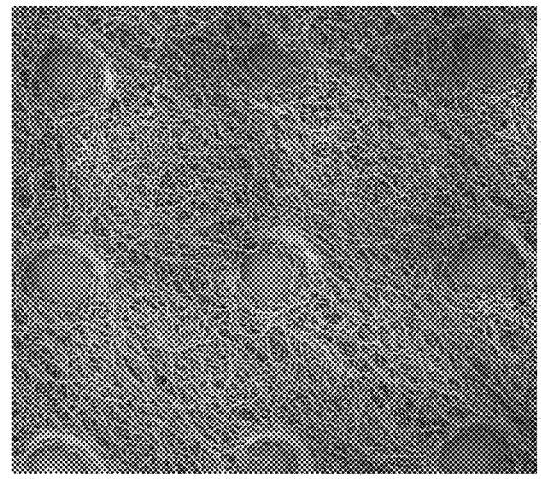
FIG. 31 is a top view of an example three-dimensional, apertured substrate produced by the first and second rolls 8, 10 of FIG. 1.
Figure 32:
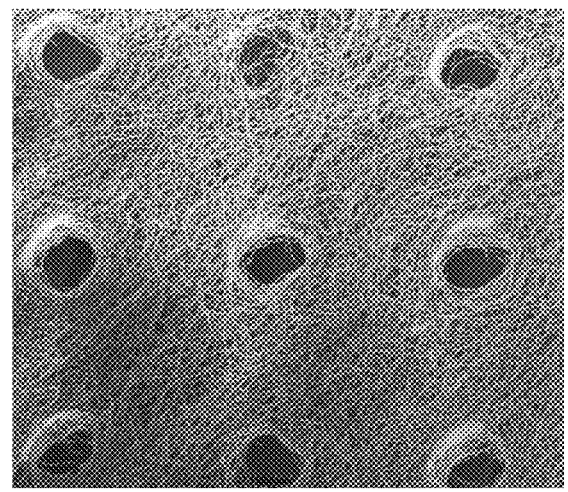
FIG. 32 is a back view of the example three-dimensional, apertured substrate of FIG. 31.
Figure 33:
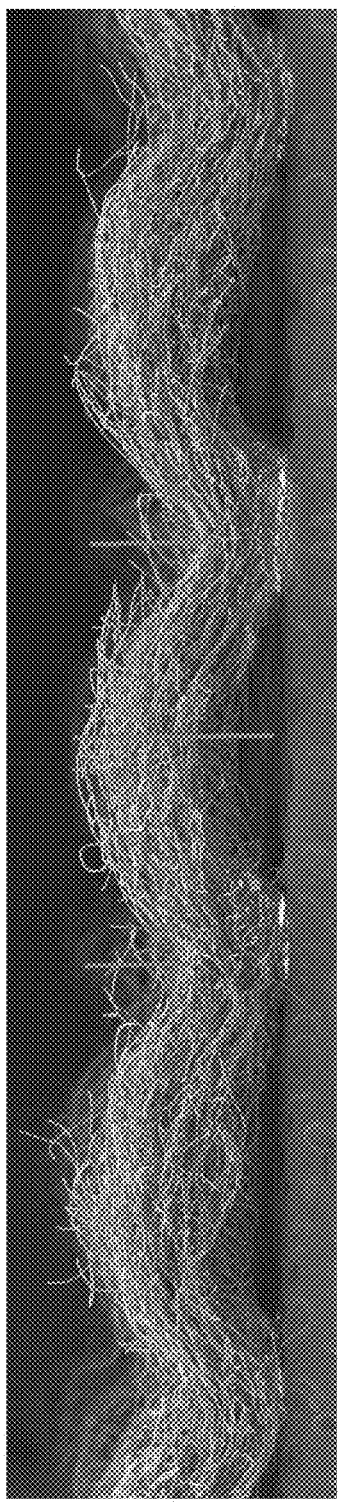
FIG. 33 is a cross-sectional view taken through the example three-dimensional, apertured substrate of FIG. 31.

FIG. 30 is a top perspective view of an example three-dimensional, apertured substrate produced by the first and second rolls 8, 10 of the present disclosure. FIG. 31 is a top view of an example three-dimensional, apertured substrate produced by the first and second rolls 8, 10 of the present disclosure. FIG. 32 is a back view of the example three-dimensional, apertured substrate of FIG. 31. FIG. 33 is a cross-sectional view taken through the example three-dimensional, apertured substrate of FIG. 31.

Figure 34:
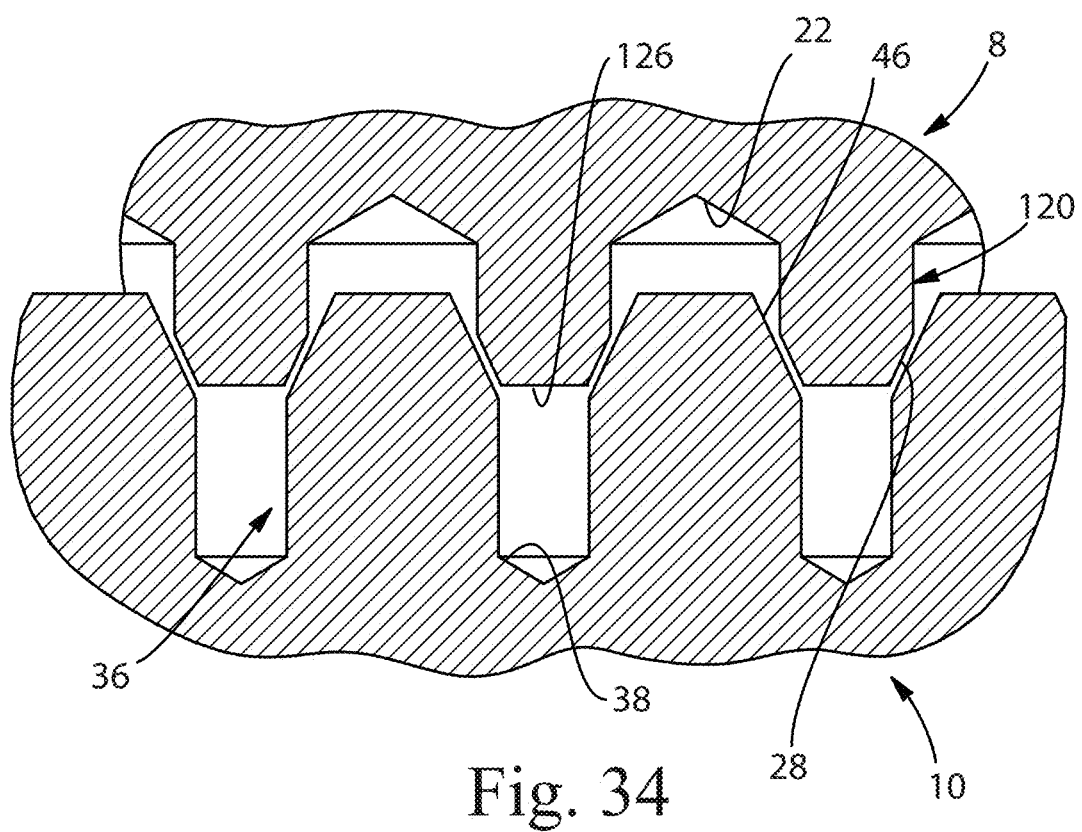
FIG. 34 is a simplified schematic cross-sectional example illustration of the rolls 8, 10 that are configured primarily for creating three-dimensional elements and compressed regions in the precursor substrate 4 and not apertures.
Figure 36:
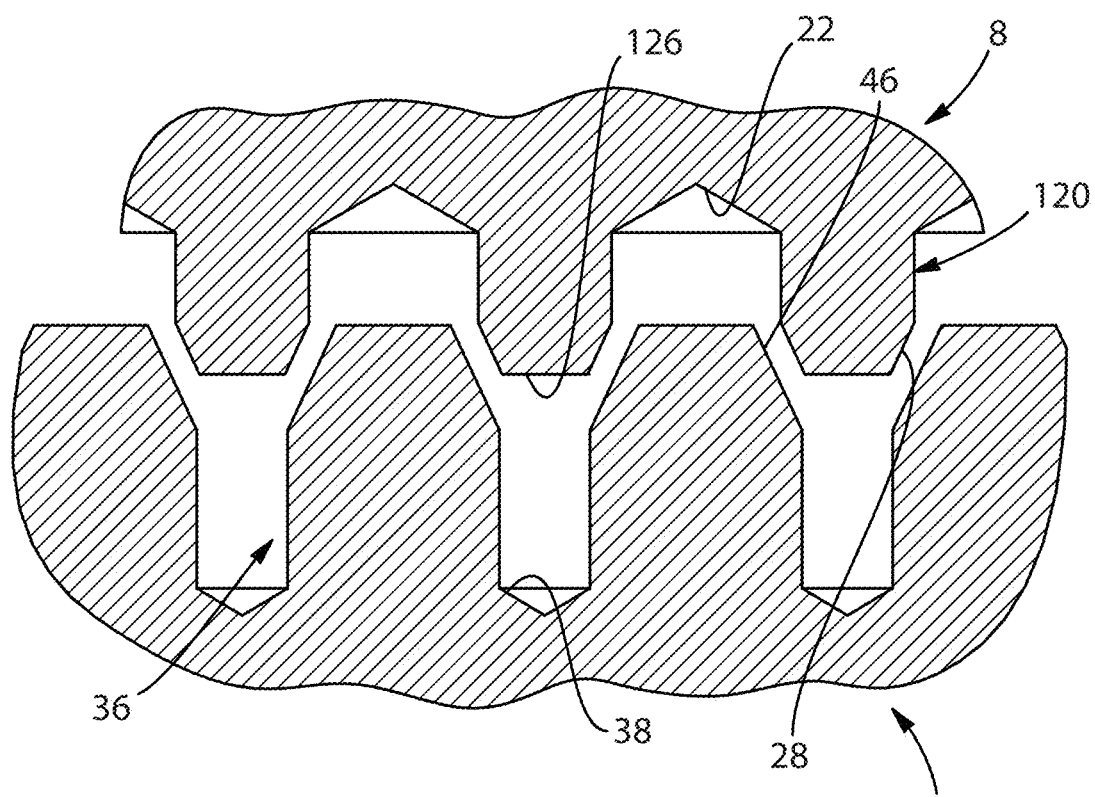
FIG. 36 is a simplified schematic cross-sectional example illustration of the rolls 8, 10 that are configured primarily for creating three-dimensional elements and compressed regions in the precursor substrate 4 and not apertures.

FIG. 34 illustrates a simplified schematic cross-sectional example illustration of the rolls 8, 10 that are configured primarily for creating three-dimensional elements and compressed regions in the precursor substrate 4 and not apertures. In FIG. 34, distal ends 126 of the first plurality of projections 120 may form flat or rounded surfaces so as to not aperture the precursor substrate. The second plurality of projections 36 and the second roll 10 generally may remain the same as described above. FIG. 36 illustrates a simplified schematic cross-sectional example illustration of the rolls 8, 10 of FIG. 34 with less engagement with each other. This level of engagement may be used for thicker substrates, for example, or when less compression is desired.

Figure 35:
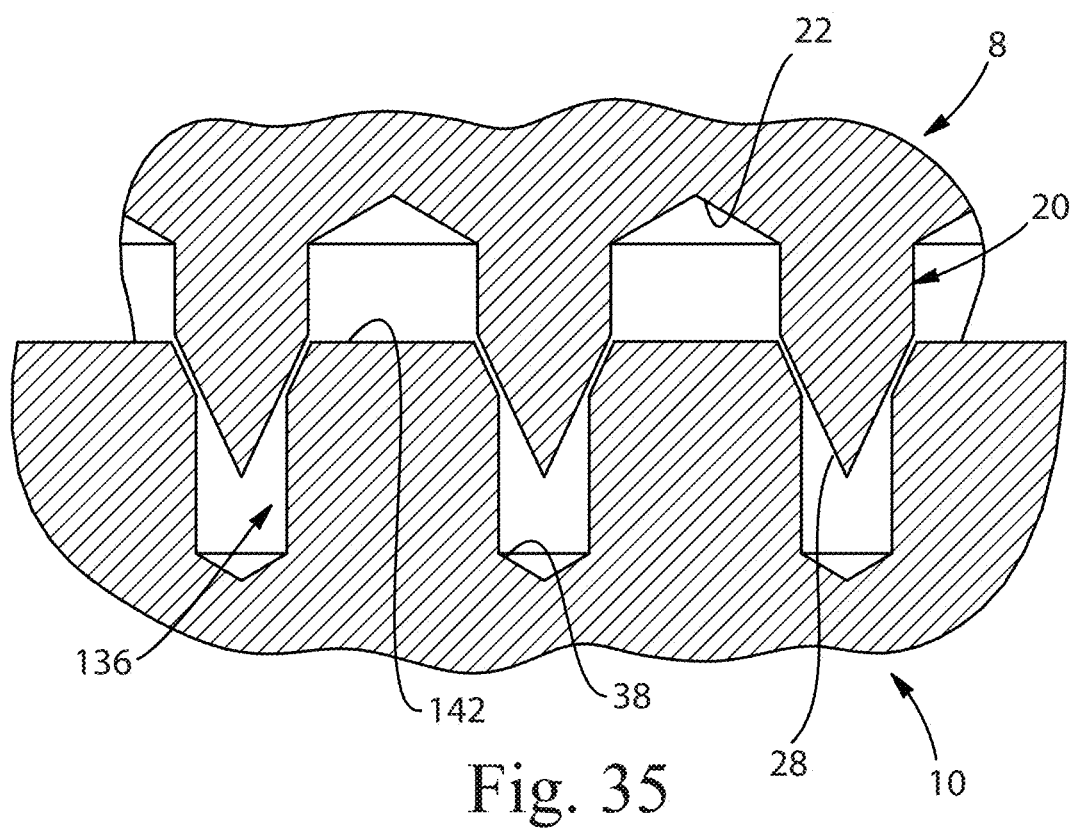
FIG. 35 is a simplified schematic cross-sectional example illustration of the rolls 8, 10 that are configured primarily for creating apertures and compressed regions in the precursor substrate 4 and not three-dimensional elements or more limited (e.g., less height) three dimensional features compared to the rolls 8, 10 of FIG. 4.
Figure 37:
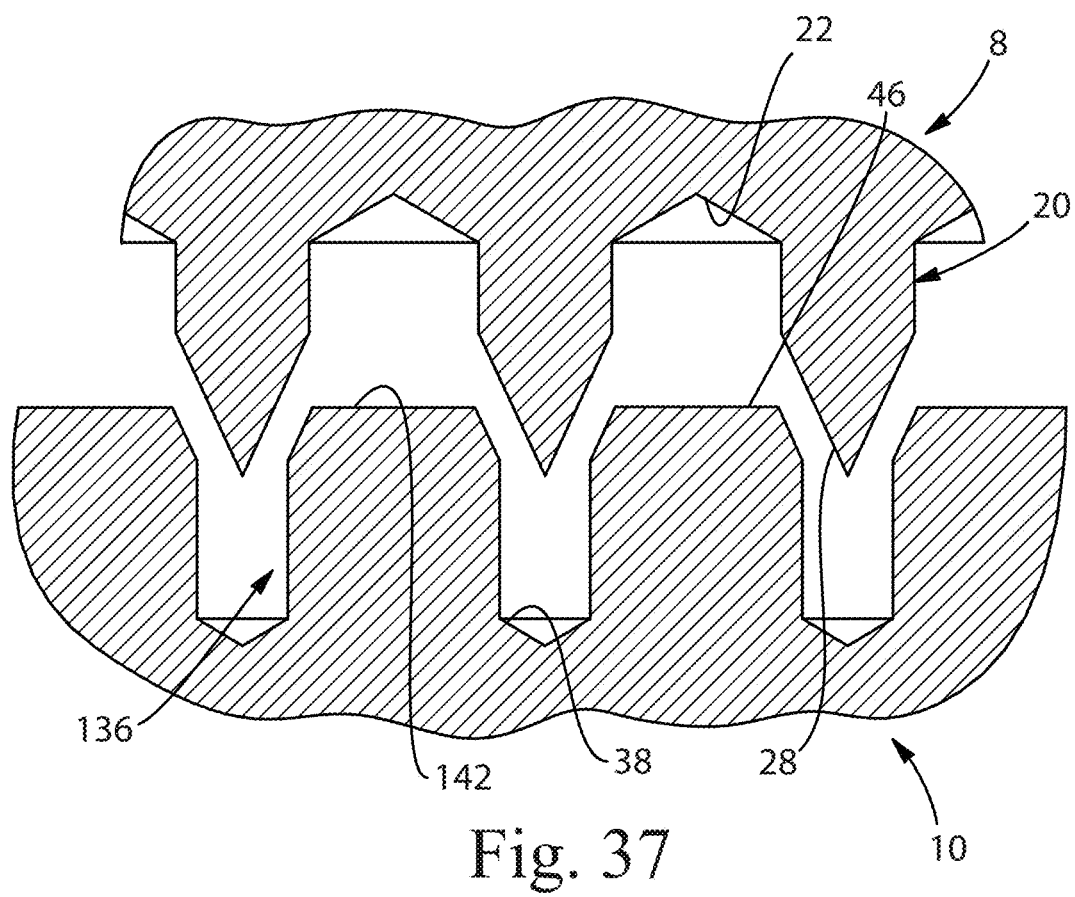
FIG. 37 is a simplified schematic cross-sectional example illustration of the rolls 8, 10 that are configured primarily for creating apertures and compressed regions in the precursor substrate 4 and not three-dimensional elements or more limited (e.g., less height) three dimensional features compared to the rolls 8, 10 of FIG. 4 and FIG. 35.

FIG. 35 illustrates a simplified schematic cross-sectional example illustration of the rolls 8, 10 that are configured primarily for creating apertures and compressed regions in the precursor substrate 4 and not three-dimensional elements or more limited (e.g., less height) three dimensional features compared to the rolls 8, 10 of FIG. 4. In FIG. 35, second distal ends 142 of the second plurality of projections 136 may form flat or rounded surfaces, for example to eliminate three-dimensional feature formation or to reduce the height of the three-dimensional elements in the precursor substrate. The first plurality of projections 20 and the first roll 8 generally may remain the same as described above. FIG. 37 illustrates a simplified schematic cross-sectional example illustration of the rolls 8, 10 of FIG. 35 with less engagement with each other. This level of engagement may be used for thicker substrates, for example, or when less compression and/or smaller apertures are desired.

Figure 38:
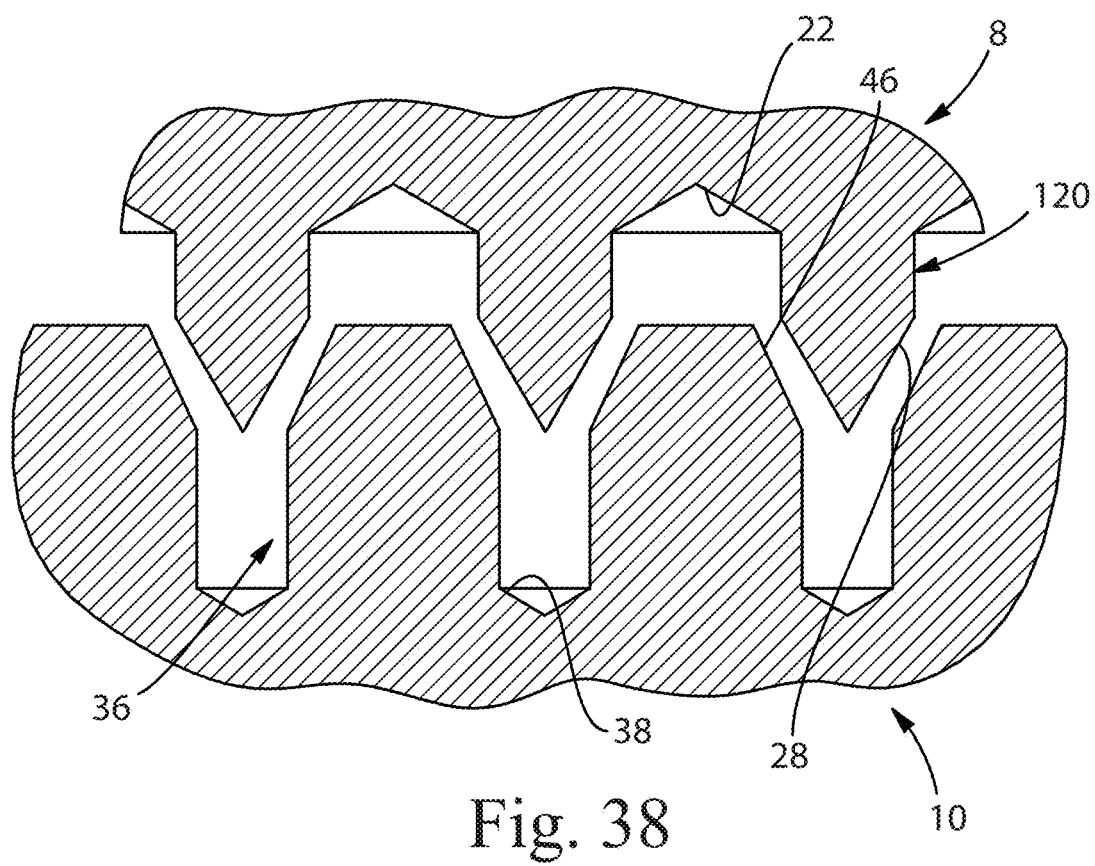
FIG. 38 is a simplified schematic cross-sectional example illustration of the rolls 8, 10 that are configured for creating apertures and three-dimensional elements in the precursor substrate 4, but not compressed regions.

FIG. 38 illustrates a simplified schematic cross-sectional example illustration of the rolls 8, 10, like FIG. 4, but with more separation between the rolls 8, 10. In such an instance, the rolls 8, 10 may be set apart from each other such that only apertures and three-dimensional elements are formed in the precursor substrate 2, without compressed regions being formed between the side walls 28 and the shoulders 46. In some instances, portions of the precursor substrate 4 may be slightly compressed between the side walls 28 and the shoulders 46, but not to the extent of compression that would result from the rolls 8, 10 of FIG. 4. As such, the center-to-center distance of the first central longitudinal axis 32 of the first roll may be adjusted with respect to the second central longitudinal axis 32 of the second roll to determine the amount of compression in portions of the precursor substrate 4 between the side walls 28 and the shoulders 46. In some instances, more compression may be desired and, in other instances, less compression may be desired. The thickness of the precursor substrate 4 may also be a factor to consider in setting the center-to-center distance of the rolls 8, 10. This concept of setting the center-to-center distance of the rolls may also apply to any of the other example roll configurations set forth herein.

Figure 39:
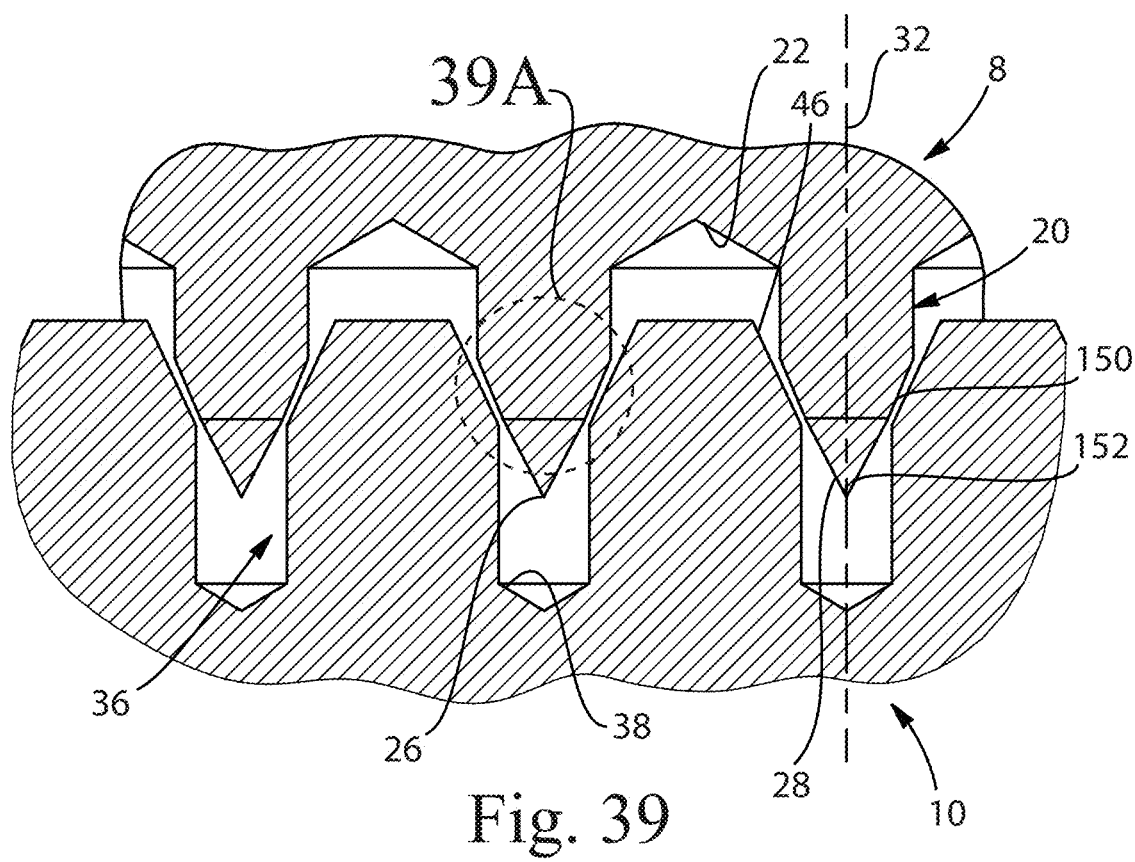
FIG. 39 is a simplified schematic cross-sectional illustration of a portion of a first roll of intermeshed with a portion of a second roll.
Figure 39A:
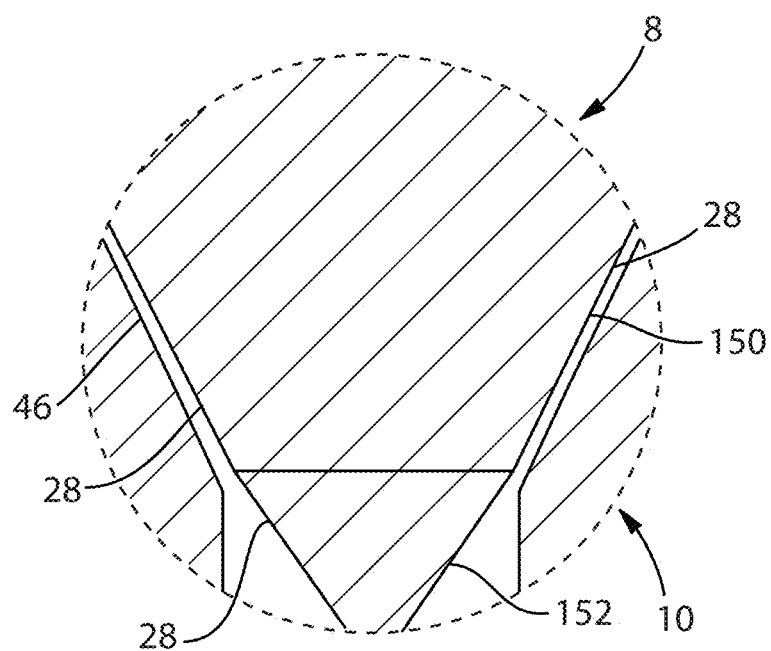
FIG. 39A is an exploded view of region 39A in FIG. 39.

FIG. 39 illustrates a simplified schematic cross-sectional example illustration of a portion of a first roll 8 intermeshed with a portion of a second roll 10. FIG. 39A is an exploded view of region 39A in FIG. 39. The second roll 10 may be substantially the same as, or the same as, the second roll 10 of FIG. 37 or 38. At least some of, or all of, the projections 20 may comprise first distal portions 24 comprising elongated aperturing structures comprising side walls 28. The side walls 28 may have a first portion 150 having a first angle and a second portion 152 having a second angle. The angles are measured relative to a central longitudinal axis 32 (see e.g., FIGS. 9A and 39) of a projection 20. The second portion 152 may be more proximal to the first distal end 26 or point than the first portion 150. The first angle may be lower than or steeper than the second angle. The first angle of the first portion 150 may be in the range of about 20 degrees to about 50 degrees, about 25 degrees to about 40 degrees, about 30 degrees to about 40 degrees, about 35 degrees, about 36 degrees, or about 37 degrees, specifically reciting all 0.1 degree increments within the specified ranges and all ranges formed therein or thereby. The second angle of the second portion 152 may be in the range of about 30 degrees to about 60 degrees, about 35 degrees to about 55 degrees, about 40 degrees to about 50 degrees, about 46 degrees, about 47 degrees, or about 48 degrees, specifically reciting all 0.1 degree increments within the specified ranges and all ranges formed therein or thereby. By having a smaller angle or steeper sidewall in the first portion 150 and a larger angle and less steep sidewall in the second portion 152, the overall longitudinal length of the projections 20 may be shorter compared to a projection having a first distal portion with only one angle. Shorter projections allow for easier engagement between the first and second rolls 8, 10. Any of the example rolls configured for aperturing may have the features of the first plurality of projections 20 described in this paragraph in reference to FIGS. 39 and 39A. Further, the features of the first plurality of projections 20 may be used when merely making apertures and not there-dimensional projections (e.g., FIGS. 35 and 37).

The shoulders 46 may taper inwards toward the point of the first plurality of projections 20 or may have the same angle as the first portion 150.

The various rolls may be formed by materials that have good thermal conductivity and that are easy to machine. Example materials include cooper, aluminum, and brass, for example. In some instances, the rolls may be steel or hardened steel. The rolls may have various surface coatings to reduce wear.

Figure 40:
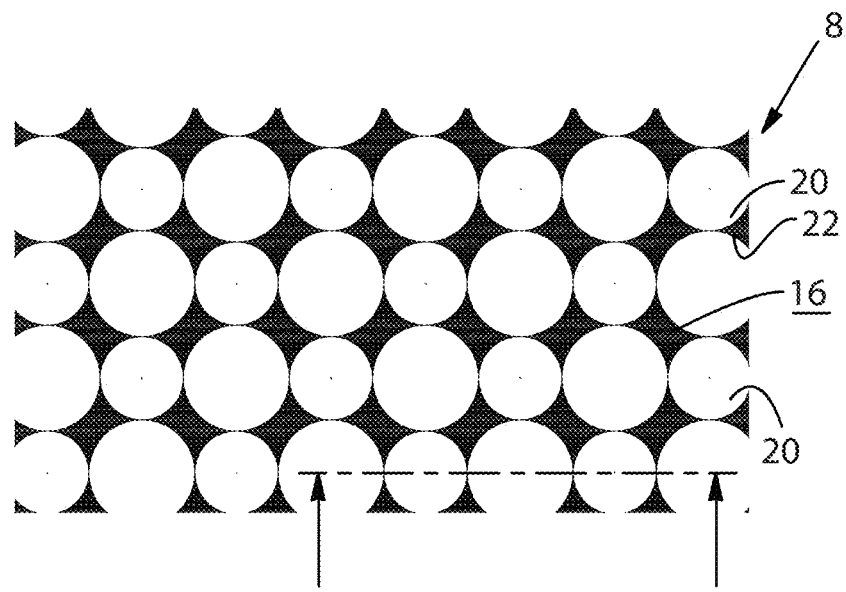
FIG. 40 is a top view of a portion of an example first roll 8.
Figure 40A:
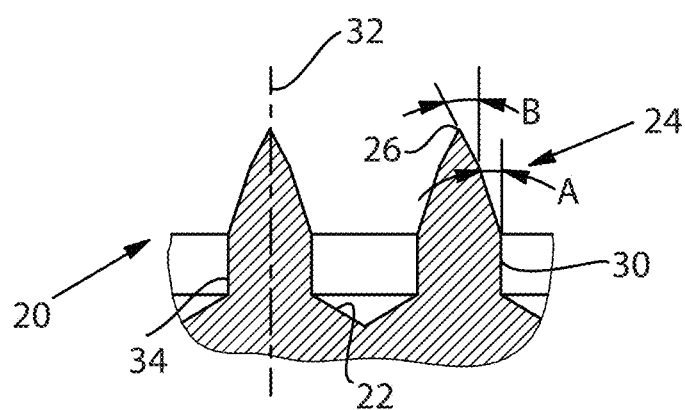
FIG. 40A is a cross-sectional view of a portion of the first roll 8 taken about line 40A-40A of FIG. 40.

FIG. 40 is a top view of a portion of an example first roll 8 of the pair of rolls of FIG. 1. FIG. 40A is a cross-sectional view of a portion of the first roll 8 of the pair of rolls of FIG. 1 taken about line 40A-40A of FIG. 40. The first roll 8 may comprise a first plurality of projections 20, a first plurality of recesses 22, and a first radial outer surface 16. The first plurality of projections 20 may each comprise a base 30 comprising side walls 34. At least some of, or most of, the first plurality of projections 20 may each comprise first distal portions 24 comprising first distal ends 26 forming a point. The term "point" is defined herein. The first plurality of projections 20 may each comprise a central longitudinal axis 32. The first distal portions 24 may comprise side walls 28. The side walls 28 may have a first angle, A, in a first portion proximate to the base 30 and a second angle, B, in a second portion distal from the base 30. Both the first and second angles are relative to the central longitudinal axis 32. The first angle, A, may be in the range of about 5 degrees to about 60 degrees, about 10 degrees to about 50 degrees, about 10 degrees to about 40 degrees, about 10 degrees to about 35 degrees, about 10 degrees to about 30 degrees, about 10 degrees to about 25 degrees, about 15 degrees to about 21 degrees, or about 18 degrees, specifically reciting all 0.1 degrees increments in the specified ranges and all ranges formed therein or thereby. The second angle, B, may be in the range of about 15 degrees to about 70 degrees, about 15 degrees to about 50 degrees, about 15 degrees to about 40 degrees, about 20 degrees to about 40 degrees, about 25 degrees to about 35 degrees, about 27 degrees to about 29 degrees, or about 28 degrees, specifically reciting all 0.1 degrees increments in the specified ranges and all ranges formed therein or thereby.

Figure 41:
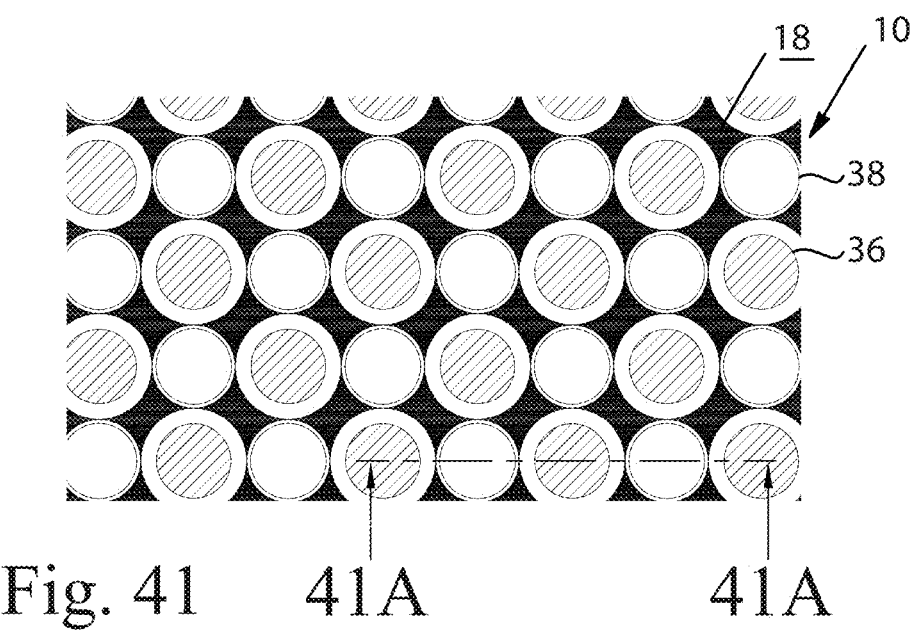
FIG. 41 is a top view of a portion of an example second roll 10.
Figure 41A:
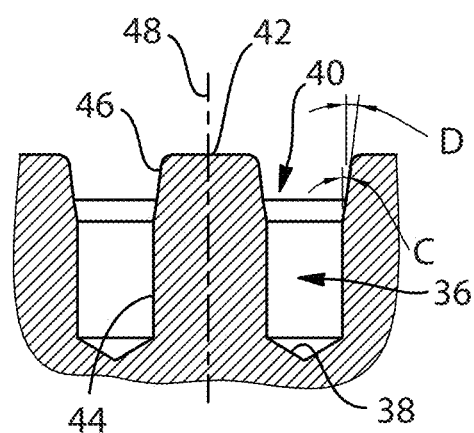
FIG. 41A is a cross-sectional view of a portion of the second roll 10 taken about line 41A-41A of FIG. 41.

FIG. 41 is a top view of a portion of an example second roll 10 of the pair of rolls of FIG. 1. FIG. 41A is a cross-sectional view of a portion of the second roll 10 taken about line 41A-41A of FIG. 41. The second roll 10 may comprise a second plurality of projections 36, a second plurality of recesses 38, and a second radial outer surface 18. The second plurality of projections 36 may comprise a base 44 comprising side walls. At least some of, or most of, the second plurality of projections 36 may each comprise second distal portions 40 comprising second distal ends 42. The second distal ends may be flat or substantially flat, or may comprise arcuate portions or dome-like structures. The second plurality of projections 36 may each comprise a central longitudinal axis 48. The second distal portions 40 may comprise shoulders 46. The shoulders 46 may have a first angle, C, in a first portion proximate to the base 44 and a second angle, D, in a second portion distal from the base 44. Both the first and second angles are relative to the central longitudinal axis 48. The first angle, C, may be in the range of about 2 degrees to about 50 degrees, about 2 degrees to about 40 degrees, about 2 degrees to about 30 degrees, about 2 degrees to about 20 degrees, about 5 degrees to about 20 degrees, about 5 degrees to about 15 degrees, about 8 degrees to about 12 degrees, or about 10 degrees, specifically reciting all 0.1 degrees increments in the specified ranges and all ranges formed therein or thereby. The second angle, D, may be in the range of about 2 degrees to about 50 degrees, about 2 degrees to about 40 degrees, about 2 degrees to about 30 degrees, about 2 degrees to about 20 degrees, about 3 degrees to about 20 degrees, about 3 degrees to about 15 degrees, about 5 degrees to about 10 degrees, or about 7 degrees, specifically reciting all 0.1 degrees increments in the specified ranges and all ranges formed therein or thereby.

Upon information and belief, it may be desirable, in some instances, to have the first angle, A, and the first angle, C, to be different to allow for more concentrated (smaller) compressed regions formed in the substrates intermediate the shoulders 46 and the side walls 28 of the first distal portions 24. Stated another way, having the first angle, A, and the first angle, C, be different may cause the compressed regions to form ring-like structures compared to partial cone-like structures when the angles A and C are the same, or substantially the same (e.g., within a few degrees). If the first angle, A, and the first angle, C, are the same or substantially the same, the compressed regions formed in the substrates may be larger, thereby potentially impacting softness of the formed substrates. Compressed regions having ring-like structures may provide improved softness of the formed substrates.

Figure 42:
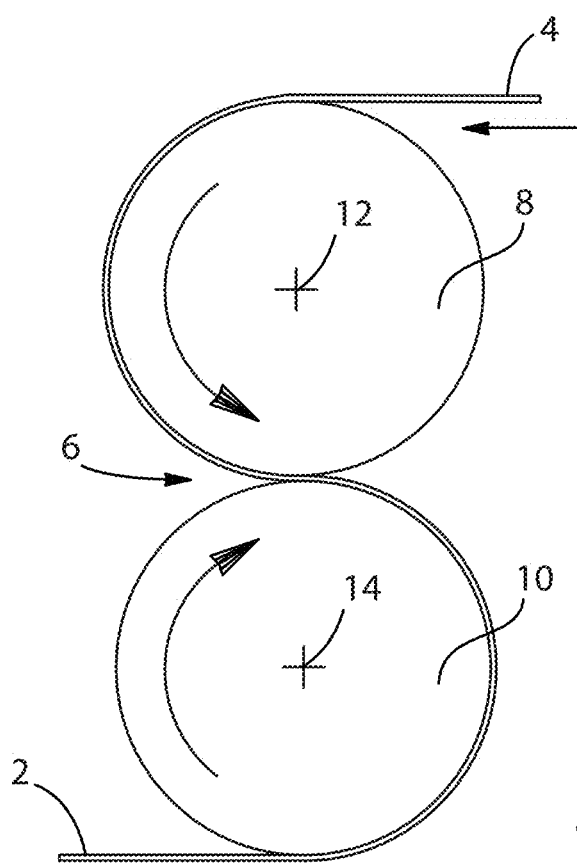
FIG. 42 is an example of a wrapping configuration for the substrate or substrates passing through the various first and second rolls of the present disclosure.

FIG. 42 is an example of a wrapping configuration for the substrate or substrates passing through the various first and second rolls 8, 10 of the present disclosure. The first roll 8 may rotate about the first rotational axis 12 in the direction indicated by the arrow. The second roll 10 may rotate about the second rotational axis 14 in the direction indicated by the arrow. The precursor substrate 4 is conveyed partially around the first roll 8 before entering the nip 6. This allows the precursor substrate 4 to be locked in place on the first roll 8 because of the first plurality of projections 20 and the first distal ends 26 thereof piercing through the precursor substrate 4. The precursor substrate 4 is then conveyed through the nip 6 and then is conveyed at least partially around the second roll 10 such that the formed substrate 2 remains engaged with the second plurality of projections 36 on the second roll 10 to lock the three-dimensional structure into the formed substrate 2. This type of wrapping configuration may be known as an "S-wrap" configuration. As discussed herein, the first and second rolls 8, 10 and/or the precursor substrate 4 may be heated to aid in formation of the substrate 2. Any of the first and second rolls described herein may use this wrapping configuration or use the example wrapping configuration of FIG. 43 or may be conveyed through the nip as illustrated as in example in FIG. 1, for example. Other wrapping configurations are also within the scope of the present disclosure.

Figure 43:
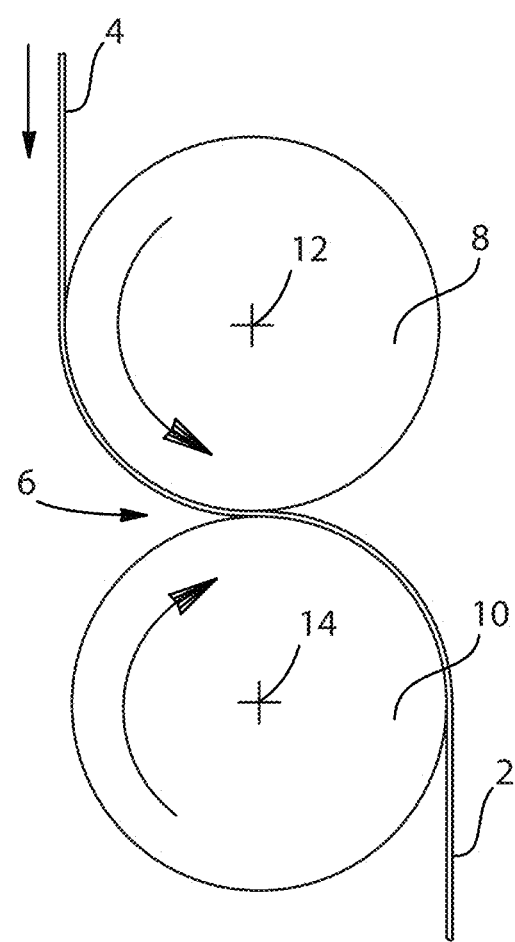
FIG. 43 is another example of a wrapping configuration for the substrate or substrates passing through various the first and second rolls of the present disclosure.

FIG. 43 is another example of a wrapping configuration for the substrate or substrates passing through various the first and second rolls 8, 10 of the present disclosure. The first roll 8 may rotate about the first rotational axis 12 in the direction indicated by the arrow. The second roll 10 may rotate about the second rotational axis 14 in the direction indicated by the arrow. The precursor substrate 4 is conveyed partially around the first roll 8 before entering the nip 6. This allows the precursor substrate 4 to be locked in place on the first roll 8 because of the first plurality of projections 20 and the first distal ends 26 thereof piercing through the precursor substrate 4. The precursor substrate 4 is then conveyed through the nip 6 and then is conveyed at least partially around the second roll 10 such that the formed substrate 2 remains engaged with the second plurality of projections 36 on the second roll 10 to lock the three-dimensional structure into the formed substrate 2. As discussed herein, the first and second rolls 8, 10 and/or the precursor substrate may be heated to aid in formation of the substrate 2.

Methods

Methods of making the three-dimensional, and optionally apertured substrate on an absorbent article manufacturing line will now be discussed.

Methods of making three-dimensional, apertured substrates on an absorbent article manufacturing line are provided. As mentioned herein the substrates may comprise only apertures and compressed regions or may comprise only three-dimensional elements and compressed regions. The method may comprise conveying a precursor substrate in a machine direction on the absorbent article manufacturing line, providing a first roll having a first rotational axis, and providing a second roll having a second rotational axis. The first rotational axis and the second rotational axis may be positioned generally parallel to each other to form a nip between the first and second rolls. The first roll may comprise a first radial outer surface, and a first plurality of projections extending at least partially outwardly from the first radial outer surface. The first plurality of projections may be configured to form apertures in the precursor substrate. The first roll may comprise a first plurality of recesses defined in the first radial outer surface, and first distal portions of at least some of the first plurality of projections forming elongated aperturing structures. The elongated aperturing structures may comprise side walls. First distal ends of the at least some of the first plurality of projections may form a point. The first plurality of projections may each have a first central longitudinal axis extending through the point. Portions of the side walls may have a first angle (e.g., angle A FIG. 40A), relative to the first central longitudinal axis, in the range of about 5 degrees to about 40 degrees, about 10 degrees to about 30 degrees, or about 15 degrees to about 25 degrees. The second roll may comprise a second radial outer surface, and a second plurality of projections extending at least partially outwardly from the second radial outer surface. The second plurality of projections may be configured to form three-dimensional elements in the precursor substrate. The second plurality of projections may comprise second distal portions and second distal ends. A second plurality of recesses may be defined in the second radial outer surface. At least some of the second distal portions may comprise shoulders positioned intermediate bases and the distal ends. The second plurality of projections may have a second central longitudinal axis. Portions of the shoulders may have a second angle (e.g., angle C, FIG. 41A), relative to the second central longitudinal axes, in the range of about 3 degrees to about 30 degrees, about 3 to about 20 degrees, about 5 degrees to about 20 degrees, or about 5 degrees to about 15 degrees. The method may comprise rotating the first roll in a first direction about the first rotational axis, rotating the second roll in a second, opposite direction about the second rotational axis, intermeshingly engaging portions of the first plurality of projections with portions of the second plurality of recesses in the nip, and intermeshingly engaging portions of the second plurality of projections with portions of the first plurality of recesses in the nip. The method may comprise conveying the precursor substrate through the nip and forming in the nip (all of or at least two of): (1) apertures in the precursor substrate using the at least some of the first plurality of projections and the at least some of the second plurality of recesses; (2) three-dimensional elements in the precursor substrate in areas free of the apertures using the at least some of the second plurality of projections and the at least some of the first plurality of recesses; and (3) compressed regions of the precursor substrate formed intermediate portions of the side walls and portions of the shoulders.

The method may comprise compressing portions of the three-dimensional elements intermediate the portions of the side walls and the portions of the shoulders. The second distal ends may form a flat or substantially flat surface or may form an arcuate surface or dome-like surface. The side walls may surround the first central longitudinal axis. In other instances, the side walls may not fully surround the first central longitudinal axis. The shoulders may surround the second central longitudinal axis. In other instances, the shoulders may not fully surround the second central longitudinal axis.

At least some of the first plurality of projections may comprise a base having a first width, taken in a direction perpendicular to the machine direction. The bases of the at least some of the second plurality of projections may have a second width, taken in a direction perpendicular to the machine direction. The second width may be different than the first width. At least some of the first plurality of recesses may have a third width, taken in a direction perpendicular to the machine direction. At least some of the second plurality of recesses may have a fourth width, taken in a direction perpendicular to the machine direction. The third width may be different than the fourth width.

The method may comprise heating the precursor substrate prior to the precursor substrate being conveyed through the nip and cooling the precursor substrate downstream of the nip. The method may comprise heating the first roll and/or the second roll and cooling the precursor substrate downstream of the nip. In some cases, it may be desirable to heat the precursor substrate before the nip and heat the first and/or second rolls, while still cooling after the nip. Cooling may occur merely by using ambient air or by providing actual chilled air or rolls etc.

The method may comprise only contacting a central strip of the precursor substrate with portions of the first plurality of projections, portions of the first plurality of recesses, portions of the second plurality of projections, and portions of the second plurality of recesses within the nip. The central strip may be is continuous in the machine direction. The method may comprise stretching the precursor substrate in a cross-machine direction only in portions outside of the central strip.

The method may comprise conveying a second precursor substrate in the machine direction under or over, but in contact with, the precursor substrate. The second precursor substrate may be the same as or different than the precursor substrate in basis weight, material, contact angle, density, fiber type, color, or other properties. The precursor substrate may have a first width, taken in a direction perpendicular to the machine direction. The second precursor substrate may have a second width, taken in the direction perpendicular to the machine direction. The first width may be larger than the second width. The method may comprise contacting the precursor substrate and the second precursor substrate with portions of the first plurality of projections, portions of the first plurality of recesses, portions of the second plurality of projections, and portions of the second plurality of recesses in the nip substantially only or only where the precursor substrate overlaps with the second precursor substrate. The method may comprise stretching the precursor substrate in a cross-machine direction where the precursor substrate is free of overlap with the second precursor substrate.

The method may comprise cutting the precursor substrate to a pitch for an absorbent article topsheet after the precursor substrate is conveyed through the nip. In some instances, the method may comprise cutting the precursor substrate and the second precursor substrate to a pitch for an absorbent article topsheet after the precursor substrate and the second precursor substrate are conveyed through the nip.

The compressed regions may be formed on the three-dimensional elements or may be formed at least partially around perimeters of the apertures.

The method may comprise wrapping the precursor substrate at least partially around the first roll before conveying the precursor substrate through the nip and wrapping the precursor substrate at least partially around the second roll after conveying the precursor substrate through the nip.

A method may comprise conveying a precursor substrate in a machine direction on the absorbent article manufacturing line, providing a first roll having a first rotational axis, and providing a second roll having a second rotational axis. The first rotational axis and the second rotational axis may be positioned generally parallel to each other to form a nip between the first and second rolls. The first roll may comprise a first radial outer surface, a first plurality of projections extending at least partially outwardly from the first radial outer surface. The first plurality of projections may be configured to form apertures in the precursor substrate (or merely three-dimensional elements). The first roll may comprise a first plurality of recesses defined in the first radial outer surface and first distal portions of at least some of the first plurality of projections forming elongated aperturing structures. The elongated aperturing structures comprise side walls. The first roll may comprise first distal ends of the at least some of the first plurality of projections forming a point (as defined above). The first plurality of projections have a first central longitudinal axis extending through the point. The side walls may have a first angle, relative to the first central longitudinal axes, in the range of about 30 degrees to about 70 degrees (or other ranges set forth herein). The second roll may comprise a second radial outer surface and a second plurality of projections extending at least partially outwardly from the second radial outer surface. The second plurality of projections are configured to form three-dimensional elements in the precursor substrate. The second plurality of projections may comprise second distal portions and second distal ends. The second distal ends may form a flat or substantially flat surface or may comprise a dome-like surface, for example. The second roll may comprise a second plurality of recesses defined in the second radial outer surface. At least some of the second distal portions comprise shoulders positioned intermediate bases and the distal ends. The second plurality of projections have a second central longitudinal axis. The shoulders may have a second angle, relative to the second central longitudinal axes, in the range of about 20 degrees to about 80 degrees or about 30 degrees to about 70 degrees (or other ranges as set forth herein). The first angle may be within +/−5 degrees of the second angle. The method may comprise rotating the first roll in a first direction about the first rotational axis, rotating the second roll in a second, opposite direction about the second rotational axis, intermeshingly engaging portions of the first plurality of projections with portions of the second plurality of recesses in the nip, and intermeshingly engaging portions of the second plurality of projections with portions of the first plurality of recesses in the nip, conveying the precursor substrate through the nip. The method may comprise forming in the nip apertures in the precursor substrate using the at least some of the first plurality of projections and the at least some of the second plurality of recesses, three-dimensional elements in the precursor substrate in areas free of the apertures using the at least some of the second plurality of projections and the at least some of the first plurality of recesses, and compressed regions in the three-dimensional elements of the precursor substrate formed intermediate portions of the side walls and portions of the shoulders.

The method may comprise comprising compressing or densifying portions of the three-dimensional elements intermediate the portions of the side walls and the portions of the shoulders. The first angle may be within +/−3, degrees or +/−1 degrees (or other ranges set forth herein) of the second angle. In some instances, the first angle may be substantially the same as, or the same as, the second angle.

The side walls of the first distal ends may surround the first central longitudinal axis and the shoulders may surround the second central longitudinal axis. In another instance, the side walls of the first distal ends may not, or do not, fully surround the first central longitudinal axis and the shoulders may not, or do not, fully surround the second central longitudinal.

The method may comprise applying a treatment to the precursor substrate after the precursor substrate is conveyed through the nip. The method may comprise heating the precursor substrate prior to the substrate being conveyed through the nip and/or heating the first roll and/or the second roll. The method may comprise heating the precursor substrate in the nip. The method may also comprise cooling the precursor substrate in the nip or downstream of the nip.

Pair of Rolls

Paragraph 1. A pair of rolls for making a three-dimensional, apertured substrate on an absorbent article manufacturing line, the pair of rolls comprising:

a first roll having a first rotational axis; and a second roll having a second rotational axis, wherein the first rotational axis and the second rotational axis are positioned generally parallel to each other to form a nip between the first and second rolls;

wherein the first roll comprises:
a first radial outer surface;
a first plurality of projections extending at least partially outwardly from the first radial outer surface, wherein the first plurality of projections are configured to form apertures in the substrate; and
a first plurality of recesses defined in the first radial outer surface;
wherein at least some of the first plurality of projections comprise first distal portions comprising elongated aperturing structures, wherein first distal ends of the first distal portions form a point, and wherein the elongated aperturing structures comprise side walls;
wherein the first plurality of projections each comprise a first central longitudinal axis extending in a direction perpendicular to the first rotation axis and intersecting the point, and wherein portions of the side walls have a first angle, relative to the first central longitudinal axis, in the range of about 5 degrees to about 40 degrees;
wherein the second roll comprises:
a second radial outer surface at least partially outwardly from the second radial outer surface, wherein the second plurality of projections are configured to form three-dimensional elements in the substrate; and
a second plurality of recesses defined in the second radial outer surface; and
at least some of the second plurality of projections comprise second distal portions and second distal ends;
wherein the at least some of the second distal portions comprise shoulders positioned intermediate bases of the second plurality of projections and the second distal ends;
wherein the second plurality of projections each comprise a second central longitudinal axis extending in a direction perpendicular to the second rotation axis, and wherein portions of the shoulders have a second angle, relative to the second central longitudinal axis, in the range of about 3 degrees to about 25 degrees;
wherein portions of the first plurality of projections are configured to intermeshingly engage portions of the second plurality of recesses; and wherein portions of the second plurality of projections are configured to intermeshingly engage portions of the first plurality of recesses.

Paragraph 2. The pair of rolls of Paragraph 1, wherein the at least some of the first plurality of projections comprise a first base having a first width, taken in a direction generally parallel to the first rotational axis, wherein the at least some of the second plurality of projections comprise a second base having a second width, taken in a direction generally parallel to the second rotational axis, and wherein the second width is greater than the first width.

Paragraph 3. The pair of rolls of Paragraph 1 or 2, wherein the at least some of the first plurality of recesses have a first width, taken in a direction generally parallel to the first rotational axis, wherein the at least some of the second plurality of recesses have a second width, taken in a direction generally parallel to the second rotational axis, and wherein the first width is greater than the second width.

Paragraph 4. The pair of rolls of any of the preceding Paragraphs, wherein the first angle is in the range of about 10 degrees to about 30 degrees, and wherein the second angle is in the range of about 3 degrees to about 20 degrees.

Paragraph 5. The pair of rolls of any of the preceding Paragraphs, wherein the second distal ends comprise a flat, substantially flat surfaces, arcuate surfaces, or arcuate portions.

Paragraph 6. The pair of rolls of Paragraph 5, comprising a beveled portion intermediate the second distal portions and the second distal ends.

Paragraph 7. The pair of rolls of any of the preceding Paragraphs, wherein the shoulders surround the second central longitudinal axes of the second plurality of projections.

Paragraph 8. The pair of rolls of any one of Paragraphs 1-6, wherein the shoulders do not fully surround the second central longitudinal axes of the second plurality of projections.

Paragraph 9. The pair of rolls of any one of the preceding Paragraphs, wherein the side walls surround the first central longitudinal axes of the first plurality of projections.

Paragraph 10. The pair of rolls of any one of Paragraphs 1-8, wherein the side walls do not fully surround the first central longitudinal axes of the first plurality of projections.

Paragraph 11. The pair of rolls of any one of the preceding Paragraphs, wherein the at least some of the projections of the first plurality of projections are surrounded by four of the recesses of the first plurality of recesses.

Paragraph 12. The pair of rolls of any one of the preceding Paragraphs, wherein the at least some of the projections of the second plurality of projections are surrounded by four of the recesses of the second plurality of recesses.

Paragraph 13. The pair of rolls of any one of the preceding Paragraphs, wherein the at least some of the first plurality of projections each comprise a base having a first width, taken in a direction parallel to the first rotational axis, wherein the at least some of the second plurality of recesses each have a second width, taken in a direction parallel to the second rotational axis, and wherein the first width is greater than the second width.

Paragraph 14. The pair of rolls of any one of the preceding Paragraphs, wherein the at least some of the second plurality of projections each comprise the base having a first width, taken in a direction parallel to the second rotational axis, wherein the at least some of the first plurality of recesses each have a second width, taken in a direction parallel to the first rotational axis, and wherein the first width is greater than the second width.

Paragraph 15. The pair of rolls of any one of the preceding Paragraphs, wherein the elongated aperturing structures comprise conical structures.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any embodiment disclosed or claimed herein or that it alone, or in any combination with any other reference or references, teaches, suggests or discloses any such embodiment. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications may be made without departing from the spirit and scope of the present disclosure. It is therefore intended to cover in the appended claims all such changes and modifications that are within the scope of this disclosure.

What is claimed is:

1. A method of making a three-dimensional, apertured substrate on an absorbent article manufacturing line, the method comprising:

conveying a precursor substrate in a machine direction on the absorbent article manufacturing line;

providing a first roll having a first rotational axis;

providing a second roll having a second rotational axis, wherein the first rotational axis and the second rotational axis are positioned generally parallel to each other to form a nip between the first and second rolls;

wherein the first roll comprises:
 a first radial outer surface;
 a first plurality of projections extending at least partially outwardly from the first radial outer surface, wherein the first plurality of projections are configured to form apertures in the precursor substrate;
 a first plurality of recesses defined in the first radial outer surface;
 first distal portions of at least some of the first plurality of projections forming elongated aperturing structures, wherein the elongated aperturing structures comprise side walls; and
 first distal ends of the at least some of the first plurality of projections forming a point;
 wherein the first plurality of projections each have a first central longitudinal axis extending through the point;

wherein the second roll comprises:
 a second radial outer surface;
 a second plurality of projections extending at least partially outwardly from the second radial outer surface, wherein the second plurality of projections are configured to form three-dimensional elements in the precursor substrate, and wherein the second plurality of projections comprise second distal portions and second distal ends;

a second plurality of recesses defined in the second radial outer surface; and wherein at least some of the second plurality of projections comprise shoulders positioned intermediate bases and the second distal ends, wherein opposite side walls of the bases are parallel to each other;

wherein the second plurality of projections have a second central longitudinal axis;

wherein the second distal ends are flat, or substantially flat;

rotating the first roll in a first direction about the first rotational axis;

rotating the second roll in a second, opposite direction about the second rotational axis;

intermeshingly engaging portions of the first plurality of projections with portions of the second plurality of recesses in the nip;

intermeshingly engaging portions of the second plurality of projections with portions of the first plurality of recesses in the nip;

conveying the precursor substrate through the nip; and forming in the nip:
apertures in the precursor substrate using the at least some of the first plurality of projections and the at least some of the second plurality of recesses;
three-dimensional elements in the precursor substrate in areas free of the apertures using the at least some of the second plurality of projections and the at least some of the first plurality of recesses; and
compressed regions of the precursor substrate formed between portions of the side walls and portions of the shoulders.

2. The method of claim 1, comprising compressing portions of the three-dimensional elements between the portions of the side walls and the portions of the shoulders.

3. The method of claim 1, wherein the side walls of the elongated aperturing structures surround the first central longitudinal axis, and wherein the shoulders surround the second central longitudinal axis.

4. The method of claim 1, wherein the at least some of the first plurality of projections comprise a base having a first width, taken in a direction perpendicular to the machine direction, wherein the bases of the at least some of the second plurality of projections have a second width, taken in a direction perpendicular to the machine direction, wherein the second width is different than the first width, wherein the at least some of the first plurality of recesses have a third width, taken in a direction perpendicular to the machine direction, wherein the at least some of the second plurality of recesses have a fourth width, taken in a direction perpendicular to the machine direction, and wherein the third width is different than the fourth width.

5. The method of claim 1, comprising:
heating the precursor substrate prior to the precursor substrate being conveyed through the nip; and
cooling the precursor substrate downstream of the nip.

6. The method of claim 1, comprising:
heating the first roll and/or the second roll; and
cooling the precursor substrate downstream of the nip.

7. The method of claim 1, comprising only contacting a central strip of the precursor substrate with portions of the first plurality of projections, portions of the first plurality of recesses, portions of the second plurality of projections, and portions of the second plurality of recesses within the nip, wherein the central strip is continuous in the machine direction.

8. The method of claim 7, comprising stretching the precursor substrate in a cross-machine direction only in portions outside of the central strip.

9. The method of claim 1, comprising conveying a second precursor substrate in the machine direction under or over, but in contact with, the precursor substrate, wherein the precursor substrate has a first width, taken in a direction perpendicular to the machine direction, wherein the second precursor substrate has a second width, taken in the direction perpendicular to the machine direction, and wherein the first width is larger than the second width.

10. The method of claim 9, comprising contacting the precursor substrate and the second precursor substrate with portions of the first plurality of projections, portions of the first plurality of recesses, portions of the second plurality of projections, and portions of the second plurality of recesses in the nip substantially only where the precursor substrate overlaps with the second precursor substrate.

11. The method of claim 10, comprising cutting the precursor substrate and the second precursor substrate to a pitch for an absorbent article topsheet after the precursor substrate and the second precursor substrate are conveyed through the nip.

12. The method of claim 10, wherein the precursor substrate is a first material, and wherein the second precursor substrate is a second, different material.

13. The method of claim 10, comprising stretching the precursor substrate in a cross-machine direction where the precursor substrate is free of overlap with the second precursor substrate.

14. The method of claim 1, comprising cutting the precursor substrate to a pitch for an absorbent article topsheet after the precursor substrate is conveyed through the nip.

15. The method of claim 1, wherein the compressed regions are formed on the three-dimensional elements or are formed at least partially around perimeters of the apertures.

16. The method of claim 1, comprising:
wrapping the precursor substrate at least partially around the first roll before conveying the precursor substrate through the nip; and
wrapping the precursor substrate at least partially around the second roll after conveying the precursor substrate through the nip.

17. The method of claim 1, wherein opposite side walls of the first plurality of recesses are parallel to each other.

18. A method of making a three-dimensional, apertured substrate on an absorbent article manufacturing line, the method comprising:
conveying a precursor substrate in a machine direction on the absorbent article manufacturing line;
providing a first roll having a first rotational axis;
providing a second roll having a second rotational axis, wherein the first rotational axis and the second rotational axis are positioned generally parallel to each other to form a nip between the first and second rolls;
wherein the first roll comprises:
a first radial outer surface;
a first plurality of projections extending at least partially outwardly from the first radial outer surface, wherein the first plurality of projections are configured to form apertures in the precursor substrate;
a first plurality of recesses defined in the first radial outer surface, wherein opposite side walls of the first plurality of recesses are parallel to each other;

first distal portions of at least some of the first plurality of projections forming elongated aperturing structures, wherein the elongated aperturing structures comprise side walls; and first distal ends of the at least some of the first plurality of projections forming a point;

wherein the first plurality of projections each have a first central longitudinal axis extending through the point;

wherein the second roll comprises:

a second radial outer surface;

a second plurality of projections extending at least partially outwardly from the second radial outer surface, wherein the second plurality of projections are configured to form three-dimensional elements in the precursor substrate, and wherein the second plurality of projections comprise second distal portions and second distal ends;

a second plurality of recesses defined in the second radial outer surface; and wherein at least some of the second plurality of projections comprise shoulders positioned intermediate bases and the second distal ends, wherein opposite side walls of the bases are parallel to each other;

wherein the second plurality of projections have a second central longitudinal axis;

wherein the second distal ends are flat, or substantially flat;

rotating the first roll in a first direction about the first rotational axis;

rotating the second roll in a second, opposite direction about the second rotational axis;

intermeshingly engaging portions of the first plurality of projections with portions of the second plurality of recesses in the nip;

intermeshingly engaging portions of the second plurality of projections with portions of the first plurality of recesses in the nip;

conveying the precursor substrate through the nip; and forming in the nip at least two of:

apertures in the precursor substrate using the at least some of the first plurality of projections and the at least some of the second plurality of recesses;

three-dimensional elements in the precursor substrate in areas free of the apertures using the at least some of the second plurality of projections and the at least some of the first plurality of recesses; and compressed regions of the precursor substrate formed between intermediate portions of the side walls and portions of the shoulders.

19. A method of making a three-dimensional, apertured substrate on an absorbent article manufacturing line, the method comprising:

conveying a precursor substrate in a machine direction on the absorbent article manufacturing line;

providing a first roll having a first rotational axis;

providing a second roll having a second rotational axis, wherein the first rotational axis and the second rotational axis are positioned generally parallel to each other to form a nip between the first and second rolls;

wherein the first roll comprises:

a first radial outer surface;

a first plurality of projections extending at least partially outwardly from the first radial outer surface, wherein the first plurality of projections are configured to form apertures in the precursor substrate;

a first plurality of recesses defined in the first radial outer surface;

first distal portions of at least some of the first plurality of projections forming elongated aperturing structures, wherein the elongated aperturing structures comprise side walls; and first distal ends of the at least some of the first plurality of projections forming a point;

wherein the first plurality of projections each have a first central longitudinal axis extending through the point;

wherein the second roll comprises:

a second radial outer surface;

a second plurality of projections extending at least partially outwardly from the second radial outer surface, wherein the second plurality of projections are configured to form three-dimensional elements in the precursor substrate, and wherein the second plurality of projections comprise second distal portions and second distal ends;

a second plurality of recesses defined in the second radial outer surface; and wherein at least some of the second plurality of projections comprise shoulders positioned intermediate bases and the second distal ends, wherein opposite side walls of the bases are parallel to each other;

wherein the second plurality of projections have a second central longitudinal axis;

wherein the second distal portions comprise distal ends that are flat, or substantially flat;

rotating the first roll in a first direction about the first rotational axis;

rotating the second roll in a second, opposite direction about the second rotational axis;

intermeshingly engaging portions of the first plurality of projections with portions of the second plurality of recesses in the nip;

intermeshingly engaging portions of the second plurality of projections with portions of the first plurality of recesses in the nip;

conveying the precursor substrate through the nip; and forming in the nip at least two of:

apertures in the precursor substrate using the at least some of the first plurality of projections and the at least some of the second plurality of recesses;

three-dimensional elements in the precursor substrate in areas free of the apertures using the at least some of the second plurality of projections and the at least some of the first plurality of recesses; and compressed regions of the precursor substrate formed between portions of the side walls and portions of the shoulders.

* * * * *